US008771718B2

(12) United States Patent
Scialdone et al.

(10) Patent No.: US 8,771,718 B2
(45) Date of Patent: *Jul. 8, 2014

(54) FORMULATED TICK AND INSECT REPELLENT COMPOSITIONS

(75) Inventors: Mark A. Scialdone, West Grove, PA (US); Irwin Palefsky, Weehawken, NJ (US)

(73) Assignee: E I du Pont de Nemours and Company, Wilmington, DE (US)

( * ) Notice: Subject to any disclaimer, the term of this patent is extended or adjusted under 35 U.S.C. 154(b) by 790 days.

This patent is subject to a terminal disclaimer.

(21) Appl. No.: 11/801,776

(22) Filed: May 10, 2007

(65) Prior Publication Data

US 2007/0264297 A1  Nov. 15, 2007

Related U.S. Application Data

(60) Provisional application No. 60/799,277, filed on May 10, 2006.

(51) Int. Cl.
*A01N 25/32* (2006.01)
*A01N 43/16* (2006.01)

(52) U.S. Cl.
USPC .... 424/406; 424/405; 424/407; 424/DIG. 10; 514/456

(58) Field of Classification Search
None
See application file for complete search history.

(56) References Cited

U.S. PATENT DOCUMENTS

| | | | |
|---|---|---|---|
| 4,062,937 A | 12/1977 | Rea | |
| 4,416,881 A | 11/1983 | McGovern | |
| 4,476,147 A | 10/1984 | Hall | |
| 4,496,467 A | 1/1985 | Munteanu | |
| 4,663,346 A * | 5/1987 | Coulston et al. | 514/456 |
| 4,869,896 A | 9/1989 | Coulston | |
| 4,913,893 A | 4/1990 | Varco | |
| 6,013,255 A | 1/2000 | Edens | |
| 6,462,015 B1 | 10/2002 | Weiss | |
| 6,524,605 B1 * | 2/2003 | Coats et al. | 424/408 |
| 6,623,694 B1 | 9/2003 | Ferguson | |
| 6,673,756 B2 * | 1/2004 | Sonnenberg et al. | 510/141 |
| 7,067,677 B2 | 6/2006 | Manzer | |
| 7,067,678 B2 * | 6/2006 | Scialdone | 549/283 |
| 7,232,844 B2 * | 6/2007 | Hallahan | 514/456 |
| 7,250,174 B2 * | 7/2007 | Lee et al. | 424/401 |
| 7,435,851 B2 * | 10/2008 | Scialdone | 564/189 |
| 7,820,145 B2 * | 10/2010 | Tamarkin et al. | 424/45 |
| 2001/0009925 A1 | 7/2001 | Lambino | |
| 2002/0173436 A1 | 11/2002 | Sonnenberg | |
| 2003/0062357 A1 | 4/2003 | Schneider et al. | |
| 2003/0079786 A1 | 5/2003 | Diana et al. | |
| 2003/0191047 A1 | 10/2003 | Hallahan | |
| 2003/0235601 A1 | 12/2003 | Hallahan et al. | |
| 2004/0024054 A1 | 2/2004 | Haenke | |
| 2004/0028629 A1 | 2/2004 | Cai | |
| 2004/0127553 A1 | 7/2004 | Hallahan | |
| 2005/0137252 A1 | 6/2005 | Scialdone | |
| 2005/0239875 A1 | 10/2005 | Scialdone | |
| 2006/0148842 A1 | 7/2006 | Scialdone | |
| 2006/0201391 A1 * | 9/2006 | Scialdone | 106/416 |
| 2006/0223878 A1 | 10/2006 | Scialdone | |
| 2006/0228387 A1 | 10/2006 | Scialdone | |
| 2008/0305135 A1 | 12/2008 | Kroepke | |
| 2010/0034906 A1 | 2/2010 | Gonzalez | |
| 2010/0092404 A1 | 4/2010 | Hutchenson | |
| 2010/0145077 A1 | 6/2010 | Jackson | |
| 2010/0145078 A1 | 6/2010 | Fisher | |
| 2010/0168447 A1 | 7/2010 | Hutchenson | |
| 2010/0261915 A1 | 10/2010 | Gonzalez | |

FOREIGN PATENT DOCUMENTS

| | | | |
|---|---|---|---|
| WO | WO 03/079786 A1 | | 10/2003 |
| WO | WO 2005/034626 A1 | | 4/2005 |
| WO | WO 2005/034626 | * | 7/2006 |
| WO | WO 2006/072037 A1 | | 7/2006 |
| WO | WO 2006/072039 A1 | | 7/2006 |
| WO | WO 2006/096876 A3 | | 9/2006 |
| WO | WO 2007/041306 A1 | | 4/2007 |
| WO | WO 2007/041307 A1 | | 4/2007 |

OTHER PUBLICATIONS

U.S. Appl. No. 11/314,672, filed Dec. 21, 2005, Mark Scialdone.
U.S. Appl. No. 11/314,385, filed Jun. 16, 2006, Mark Scialdone.
U.S. Appl. No. 10/405,444, filed Dec. 4, 2003, Leo E. Manzer.
U.S. Appl. No. 11/017,254, filed Dec. 20, 2004, Mark Scialdone.
U.S. Appl. No. 10/997,279, filed Jul. 1, 2005, Mark Scialdone.
U.S. Appl. No. 60/639,945, filed Dec. 29, 2004, Mark Scialdone.
U.S. Appl. No. 60/640,129, filed Dec. 29, 2004, Mark Scialdone.
Heterogeneous Catalysis for the Synthetic Chemist, Marcel Decker, New York, N.Y., 1996 (Book Not Supplied).
F. E. Regnier et al., Studies on the Composition of the Essential Oils of Three *Nepeta* Species, Phytochemistry, vol. 6:1281-1289, 1967.
Edmund J. Eisenbraun et al., (4AS,7S,7AR)-Nepetalactam and (4AS,7S,7AR)-2-[(3R,4R,4AR,7S,7AR)-Octahydro-4,7-Dimethyl-1-Oxocyclopenta[C]Pyran-3-Yi]Nepetalactam: Nitrogen Analogues of Nepetalactone and Nepetalic-Anhydride, J. Org. Chem., vol. 53:3968-3972, 1988.
M. Jefson et al., Chemical Defense of a Rove Beetle, Journal of Chemical Ecology, Jan. 1, 1983, vol. 9:159-180.
G. Schultz et al., Natural Insect Repellents: Activity Against Mosquitoes and Cockroaches, ACS Symposium Series, 2006, vol. 927:168-181.
Tanimori et. al., Total Synthesis of (+) Dihydronepetalactone, Agric. Biol. Chem., 1991, vol. 55:1181-11832.
Fleming et. al., Sterocontrol in Organic Synthesis Using Silicon-Containing Compounds, A Synthesis of (+) Dihydronepetalactone Using the SE2 Reaction of an Allysilane, J. Chem. Soc., Perkin Trans, 1998, vol. 1:2645-2649.

(Continued)

*Primary Examiner* — Neil Levy

(57) ABSTRACT

The present invention pertains to the field of tick- or insect-repellent formulated compositions containing dihydronepetalactone, a nepetalactam, a dihydronepetalactam and/or their respective derivatives, and one or more additives to provide a useful and effective means of delivering the composition in the manner and to the location as desired by the user.

13 Claims, No Drawings

(56) References Cited

OTHER PUBLICATIONS

Wolinsky et. al., Syntheses of the Dihydronepetalactones, J. Org. Chem., 1972, vol. .37:3376-3378.
International Search Report and Written Opinion in PCT/US2007/011403, Oct. 7, 2008.
G.W.K. Cavill et. al., Defensive and Other Secretions of the Australlian Cocktail Ant, Iridomyrmex Nitidiceps, Tetrahedron, 1982, vol. 38:1931-1938.
Chris Peterson et. al., Insect Repellents—Past, Present and Future, Pesticide Outlook, Aug. 2001.
Depooter et. al., The Essential Oils Five *Nepeta* Species. A Preliminary Evaluation of Their Use in Chemotaxonomy by Cluster Analysis, Flavour and Fragrance Journal, 1988, vol. 3:155-159.
Handjieva et. al., Constituents of Essential Oils From *Nepeta cataria* L., *N. grandiflora* M.B. and *N. nuda* L., J. Essential Oil Res., 1996, vol. 8:639-643.
Regnier et al, Nepetalactone and Eipnepetalactone From *Nepeta cataria* L., Phytochemistry, 1967, vol. 6:1271-1280.
T. Eisner, Science, 1964, vol. 146:1318-1320.
International Search Report Dated July 10, 2008.

* cited by examiner

FORMULATED TICK AND INSECT REPELLENT COMPOSITIONS

This application claims the benefit of U.S. Provisional Application No. 60/799,277, filed May 10, 2006, which is incorporated in its entirety as a part hereof for all purposes.

TECHNICAL FIELD

The present invention pertains to formulated compositions containing one or more plant-derived tick and/or insect repellent active ingredients.

BACKGROUND

U.S. Ser. No. 04/127,553, which is incorporated in its entirety as a part hereof for all purposes, discloses dihydronepetalactone (DHN) diastereomers derived by hydrogenation of nepetalactone, and compositions thereof, as effective repellents against ticks and/or several species of insects of particular interest to people, including mosquitoes and stable flies.

U.S. application Ser. No. 11/314,672, which is incorporated in its entirety as a part hereof for all purposes, discloses nepetalactam diastereomers, and compositions thereof, as useful tick and/or insect repellents; and U.S. application Ser. No. 11/314,385, which is incorporated in its entirety as a part hereof for all purposes, discloses dihydronepetalactam diastereomers, and compositions thereof, as useful tick and/or insect repellents.

A need still remains however for formulated compositions of all these materials that would allow consumers to easily use them for tick and/or insect repellent purposes.

SUMMARY

One embodiment of this invention is a composition of matter, or article incorporating same, that contains two or more components selected from the group consisting of a dihydronepetalactone, a derivative of a dihydronepetalactone, a nepetalactam, an N-substituted nepetalactam, a dihydronepetalactam, an N-substituted dihydronepetalactam.

A further embodiment of this invention is a formulated tick and/or insect repellent composition, or article incorporating same, that contains, as a repellent active ingredient, a component selected from the group consisting of a dihydronepetalactone, a derivative of a dihydronepetalactone, a nepetalactam, an N-substituted nepetalactam, a dihydronepetalactam, an N-substituted dihydronepetalactam, and mixtures thereof. As fabricated from such a repellent active ingredient thereof, the composition and/or article may also possess desirable perfume characteristics.

In particular, this invention further provides a topical treatment for skin, such as a fragrance or perfume, or a repellent for a tick and/or insect, that includes a repellent active ingredient as described above.

Another embodiment of this invention is a process for fabricating a tick and/or insect repellent composition, or a tick and/or insect repellent article of manufacture, by providing as the composition or article, or incorporating into the composition or article, a repellent active ingredient as described above.

Yet another embodiment of this invention is the use of a repellent active ingredient as described above, or a composition thereof, as a tick and/or insect repellent; which thus also includes an embodiment wherein, in a method of repelling ticks and/or insects, the ticks and/or insects are exposed to repellent active ingredient as described above, or a composition thereof. In particular, this invention provides a method of repelling a tick and/or insect by applying to a surface of a host for the tick and/or insect, such as the skin, hide, hair, fur or feathers of the host, a repellent active ingredient as described above.

In a further embodiment of this invention, the repellent active ingredient is a natural, plant-derived substance. In yet another embodiment, the repellent active ingredient may be admixed with one or more adjuvants or modifers typical for use in the cosmetics industry.

DETAILED DESCRIPTION

In one embodiment, this invention provides for a composition containing one or more components selected from the group consisting of dihydronepetalactone or a derivative thereof, a nepetalactam, an N-substituted nepetalactam, a dihydronepetalactam and an N-substituted dihydronepetalactam. In a preferred embodiment, the dihydronepetalactone, nepetalactam, dihydronepetalactam, or respective derivative, or mixture thereof, functions in the composition as a tick and/or insect repellent active ingredient.

The terms "dihydronepetalactone" and "DHN" shall be herein taken to encompass any stereoisomer of dihydronepetalactone, or any combination of said stereoisomers, as well as a combination thereof which may further include a derivative of DHN such as is described below. The stereoisomers of DHN are shown in FIG. 1. Of particular interest are (1S,9S,5R,6R)-5,9-dimethyl-3-oxabicyclo[4.3.0]nonan-2-one,
(1S,5S,9S,6S)-5,9-dimethyl-3-oxabicyclo[4.3.0]nonan-2-one,
(1S,9S,6S,5R)-5,9-dimethyl-3-oxabicyclo[4.3.0]nonan-2-one,
(9S,5S,1R,6R)-5,9-dimethyl-3-oxabicyclo[4.3.0]nonan-2-one, and
(9S,1R,5R,6R)-5,9-dimethyl-3-oxabicyclo[4.3.0]nonan-2-one.

The DHNs, or derivatives thereof, suitable for the practice of the invention are represented by the Formula (I)

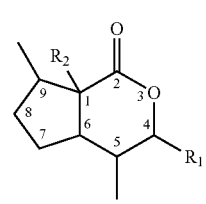

I wherein $R_1$, is hydrogen, $C_1$–$C_{20}$ alkyl or $C_6$–$C_{20}$ aryl, and $R_2$ is hydrogen or $C_1$–$C_{20}$ alkyl. Representative values for $R_1$ and/or $R_2$ may include, in addition to hydrogen, normal or branched $C_1$–$C_{20}$ alkyl such as sec-butyl or neo-pentyl, and is preferably normal $C_1$–$C_{12}$ alkyl such as methyl, ethyl, propyl, butyl, pentyl or hexyl; or $R_1$ and/or $R_2$ may be substituted or unsubstituted $C_6$–$C_{20}$ phenyl, and is preferably unsubstituted or meta- or para-substituted phenyl, where the substituent on phenyl may be normal $C_1$–$C_{12}$ alkyl or alkoxy, or halogen. In a derivative, $R_1$ and/or $R_2$ is most preferably methyl or ethyl, phenyl, or para- or meta-tolyl.

Formula (I), which does not indicate stereochemistry, shall be herein taken to encompass any stereoisomer of DHN, and any stereoisomer of a derivative of DHN, any combination of DHN stereoisomers, any combination of the stereoisomers of a DHN derivative, as well as any combination of one or more isomers of DHN together with one or more isomers of a derivative of DHN.

DHN may be prepared by direct synthesis, isolated from various natural sources, or prepared by the catalytic hydrogenation of nepetalactone. The hydrogenation of the essential oil of the nepeta (catmint) plant, or nepetalactone as extracted therefrom, is the preferred method for preparation of DHN. The nepetalactone is present in large quantity in the essential oil of the nepeta plant leaves, and is readily purified therefrom. This produces a highly desirable natural product route to the DHN.

The catalytic hydrogenation of nepetalactone to DHN may be performed according to the method in Regnier, F. E. et al, *Phytochemistry*, 6:1281~1289 (1967) wherein catalysts such as platinum oxide and palladium supported on strontium carbonate give dihydronepalactone in 24-90% yields. Preferably DHN is prepared by catalytic hydrogenation according to the method in copending U.S. patent application Ser. No. 10/405,444, which is incorporated in its entirety as a part hereof for all purposes. This method involves the use of catalytic metals such as ruthenium, rhenium, rhodium, iridium, compounds thereof, and combinations thereof, and, when used, supports such as carbon, alumina, silica, silica-alumina, titania, titania-alumina, titania-silica, barium, calcium, compounds thereof, and combinations thereof.

DHN may also be prepared by contacting nepeatalactone with an aqueous base. Suitable bases include alkali metal, alkaline earth metal, and ammonium hydroxides. Sodium, potassium, lithium, calcium, magnesium, ammonium, and tetra-alkyl ammonium hydroxides are preferred. The step of forming a basic mixture is then followed by a step of acidification with an acid to form nepetalic acid. The extracted aqueous solution, as described above, is in this step subjected to gradual acidification to a pH below about 4, preferably to a pH of about 3 or below. Acidification is preferably achieved using a strong mineral acid, such as hydrochloric, nitric, or sulfuric acids.

Nepetalic acid made as described above is then subjected to deprotonation, and to reduction of the product thereof to DHN. For this purpose, the nepetalic acid may, in one embodiment, be contacted with a non-aqueous base such as a hydride to affect deprotonation at a temperature in the range of 0° C. to about 25° C. Also useful for the deprotonation are amines, particularly triethylamine. Following the deprotonation step, the resulting salt is contacted with a reducing agent to form the DHN product. Suitable reducing agents include borohydrides and dialkylboranes. In a preferred embodiment, the separate deprotonation step is eliminated by employing an excess of the reducing agent (such as $NaBH_4$)—that is, more than one equivalent, preferably slightly more than two equivalents of the reducing agent to effect both the deprotonation and reduction in a single step. Further description of DHN, its uses and processes for making it are disclosed in copending U.S. application Ser. No. 11/017,254, which is incorporated in its entirety as a part for all purposes.

The DHN prepared from natural sources will necessarily represent a mixture of stereoisomers that may be separated into its component parts or not, depending upon the requirements of the specific application. It has been observed that variations in composition vary across different species of the nepeta genus; in certain species there is variation in composition among plants of the same species. The latter species are less preferred sources of starting material.

Fractional distillation has been found in the practice of the invention to be an effective method for both purifying nepetalactone from the essential oils, and for separating diastereomeric DHN pairs prepared therefrom. Chromatographic separations are also suitable.

DHN prepared according to any method, which may be in the form of a single stereoisomer, a diastereomeric pair, or a mixture of isomers, may be converted to a derivative thereof by substitution at position 4 as shown in Formula (I). Substitution at the C-4 position in Formula (I) may be accomplished by Grignard reagent nucleophilic addition to electrophilic nepetalic acid, the hydrated form of nepetalactone. Nepetalic acid is treated with a non-aqueous base in a deprotonation step to form a carboxylate salt. In one embodiment, for example, the nepetalic acid is treated with an alkali metal hydride, preferably KH. In this embodiment, the deprotonation step is followed by treatment with Grignard reagent to form a DHN derivative. In a further embodiment, the nepetalic acid is treated with more than one equivalent of Grignard reagent, and preferably at least two equivalents of Grignard reagent to effect formation of the derivative. This process eliminates the step of first treating nepetalic acid with a separate non-aqueous base such as an alkali metal hydride. Use of an amount of Grignard reagent in slight excess of two equivalents ensures high conversion to the desired product.

Typical Grignard reagents include, but are not limited to, those that are prepared by the union of metallic magnesium with an organic chloride, bromide or iodide usually in the presence of ether and in the complete absence of water. Suitable for use in such a process are any Grignard reagents that are reactive with aldehydes including but not limited to alkyl magnesium chlorides, alky magnesium bromides, aryl magnesium chlorides, and aryl magnesium bromides. Also included are dialkylzincs, diarylzincs and alkyllithiums and aryllithiums. Representative substituents that may be present on suitable Grignard reagents include methyl, ethyl, n-propyl, butyl, pentyl, hexyl phenyl, para- and meta-substituted phenyl including para- and meta-tolyl, and para-methoxy-phenyl. Further description of derivatives of DHN, their uses and processes for making them are disclosed in copending U.S. application Ser. No. 10/997,279, which is incorporated in its entirety as a part for all purposes.

DHN may be alternatively or further derivatized by substitution at the C-1 position in Formula (I), which may be accomplished by alkylation of the enolate of the lactone (nucleophile) with an alkylating reagent such as iodomethane (electrophile) to introduce a non-hydrogen substituent at the bridgehead. In general, bases such as lithium diisopropylamine or LDA are used for enolate generation, but many bases are suitable depending upon the particular requisites of the reaction. Alkylating agents such as alkyl halides are preferred but many alkylating agents are suitable depending upon the requisites of the specific reaction.

Nepetalactams, and a derivative thereof such as an N-substituted nepetalactams, suitable for use herein as an insect repellant active ingredient may be represented schematically by Formula (III):

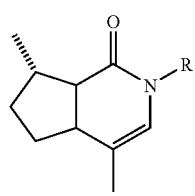

III wherein R is alkane, alkene, alkyne or aromatic.

In various embodiments, R in Formula (III) may be selected from the group consisting of: 1) H or $C_2H_5$, 2) $C_3$ to $C_{20}$ straight-chain, branched or cyclic alkane or alkene, 3) $C_3$ to $C_{20}$ straight-chain, branched or cyclic alkane or alkene comprising a heteroatom selected from the group consisting of O, N and S, 4) unsubstituted or substituted $C_6$ to $C_{20}$ aromatic, wherein the substituent is selected from the group consisting of $C_1$ to $C_{12}$ straight-chain, branched or cyclic alkane or alkene, and 5) unsubstituted or substituted $C_6$ to $C_{20}$ aromatic comprising a heteroatom selected from the group consisting of O, N and S, wherein the substituent is selected from the group consisting of $C_1$ to $C_{12}$ straight-chain, branched or cyclic alkane or alkene. The substituted or unsubstituted nepetalactam compound of Formula (III) may be a single stereoisomer of a single compound, may be a mixture of stereoisomers of a single compound, or may be a mixture of stereoisomers of compounds in which R is different.

Nepetalactams as described above may be prepared by contacting nepetalactone with anhydrous ammonia according to the method described by Eisenbraun, et al in *J. Org. Chem.*, 53:3968-3972 (1988). N-Substituted nepetalactams are then formed by reacting nepetalactam with an appropriate metal hydride to form a nepetalactam salt, followed by contacting the nepetalactam salt with an appropriate alkylating agent to form the N-substituted nepetalactam. Further description of nepetalactams and N-substituted nepetalactams, their uses and processes for making them are disclosed in copending U.S. Provisional Application Ser. No. 60/639,945, which is incorporated in its entirety as a part for all purposes.

Dihydronepetalactams, and a derivative thereof such as an N-substituted dihydronepetalactams, suitable for use herein as an insect repellant active ingredient may be represented schematically by Formula (IV):

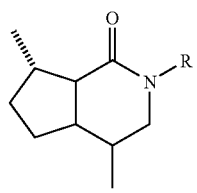

IV wherein R is alkane, alkene, alkyne or aromatic.

In various embodiments, R in the compound of Formula (IV) may be selected from the group consisting of: 1) H or $C_2H_5$, 2) $C_3$ to $C_{20}$ straight-chain, branched or cyclic alkane or alkene, 3) $C_3$ to $C_{20}$ straight-chain, branched or cyclic alkane or alkene comprising a heteroatom selected from the group consisting of O, N and S, 4) unsubstituted or substituted $C_6$ to $C_{20}$ aromatic, wherein the substituent is selected from the group consisting of $C_1$ to $C_{12}$ straight-chain, branched or cyclic alkane or alkene, and 5) unsubstituted or substituted $C_6$ to $C_{20}$ aromatic comprising a heteroatom selected from the group consisting of O, N and S, wherein the substituent is selected from the group consisting of $C_1$ to $C_{12}$ straight-chain, branched or cyclic alkane or alkene. The substituted or unsubstituted nepetalactam compound of Formula (IV) may be a single stereoisomer of a single compound, may be a mixture of stereoisomers of a single compound, or may be a mixture of stereoisomers of compounds in which R is different.

Dihydronepetalactams as described above may be prepared by alkylation of neptelactam, followed by hydrogenation, or by alkylation of dihydronepetalactam. Nepetalactam may be prepared by contacting nepetalactone with anhydrous ammonia according to the method described by Eisenbraun supra. N-Substituted dihydronepetalactams are synthesized by hydrogenation of nepetalactam to dihydronepetalactam followed by alkylation of the lactam nitrogen, or by alkylation of nepetalactam followed by hydrogenation of the N-substituted nepetalactam. Hydrogenation of nepetalactams may be effected in the presence of a suitable active metal hydrogenation catalyst such as are described in Augustine, Heterogeneous Catalysis for the Synthetic Chemist, Marcel Decker, New York, N.Y. (1996).

N-Substituted dihydronepetalactams may also be formed by reacting dihydronepetalactam with an appropriate metal hydride to form a dihydronepetalactam salt, followed by contacting the dihydronepetalactam salt with an appropriate alkylating agent to form the N-substituted dihydronepetalactam. Metal hydrides are used to generate the amide-metal salt of dihydronepetalactam. Suitable metal hydrides include, but are not limited to, potassium hydride and sodium hydride. Alkylating agents suitable for N-alkylation of the dihydronepetalactam salt include alkanyl, alkenyl, alkynyl or aryl chlorides, bromides, iodides, sulfates, mesylates, tosylates and triflates. Further description of dihydronepetalactams and N-substituted dihydronepetalactams, their uses and processes for making them are disclosed in copending U.S. Provisional Application Ser. No. 60/640,129, which is incorporated in its entirety as a part for all purposes.

In a composition as provided by this invention, the dihydronepetalactone, nepetalactam, dihydronepetalactam or respective derivative may be a single stereoisomer of one compound, a mixture of stereoisomers of one compound, respective single stereoisomers of two or more separate compounds, or a blend of respective mixtures of stereoisomers of two or more separate compounds.

In a composition as provided by this invention, a dihydronepetalactone, nepetalactam, dihydronepetalactam, and respective derivative(s), are all compounds that may be used for a multiplicity of purposes, such as use as a repellent active ingredient in an effective amount for the repellency of various insect or arthropod species, or as a fragrance compound in a perfume composition, or as a topical treatment for skin. For example, these compounds may be applied in a topical manner to the skin, hide, hair, fur or feathers of a human or animal host for an insect or arthropod, or to an inanimate host such as growing plants or crops, to impart insect or arthropod repellency or a pleasant odor or aroma. An inanimate host may also include any article of manufacture that is affected by insects, such as buildings, furniture and the like. Typically, these articles of are considered to be tick/insect-acceptable food sources or tick/insect-acceptable habitats.

A repellent or repellent composition refers to a compound or composition that drives insects or arthropods away from their preferred hosts or from tick/insect-suitable articles of manufacture. Most known repellents are not active poisons at all, but rather prevent damage to humans, animals, plants and/or articles of manufacture by making insect/arthropod food sources or living conditions unattractive or offensive. Typically, a repellent is a compound or composition that can be topically applied to a host, or can be incorporated into a tick/insect susceptible article, to deter insects/arthropods from approaching or remaining in the nearby 3-dimensional space in which the host or article exists. In either case, the effect of the repellent is to drive the insects/arthropods away from, or to reject, (1) the host, thereby minimizing the frequency of "bites" to the host, or (2) the article, thereby protecting the article from insect damage. Repellents may be in the form of gases (olfactory), liquids, or solids (gustatory).

One property that is important to overall repellent effectiveness is surface activity, as many repellents contain both polar and non-polar regions in their structure. A second property is volatility. Repellents form an unusual class of compounds where evaporation of the active ingredient from the host's skin or other surface, or from a tick/insect-repellent article, is necessary for effectiveness, as measured by the protection of the host from bites or the protection of the article from damage.

In the case of a topical insect/arthropod repellent applied to the skin, hide, hair, feathers or fur of a host, an aspect of the potency of the repellent is the extent to which the concentration of the repellent in the air space directly above the surface where applied is sufficient to repel the insects/arthropods. A desirable level of concentration of the repellent is obtained in the air space primarily from evaporation, but the rate of evaporation is affected by the rate absorption into the skin or other surface, and penetration into and through the surface is thus almost always an undesirable mode of loss of repellent from the surface. Similar considerations must be made for articles that contain a repellent, or into which a repellent has been incorporated, as a minimum concentration of repellent is required in the three-dimensional air space surrounding the article itself to obtain the desired level of protection.

In selecting a substance for use as an insect/arthropod repellent active ingredient, the inherent volatility is thus an important consideration. A variety of strategies are available, however, when needed for the purpose of attempting to increase persistence of the active while not decreasing, and preferably increasing, volatility. For example, the active can be formulated with polymers and inert ingredients to increase persistence on a surface to which applied or within an article. The presence of inert ingredients in the formulation, however, dilutes the active in the formulation as applied, and the loss from undesirably rapid evaporation must thus be balanced against the risk of simply applying too little repellent active ingredient to be effective. Alternatively, the repellent active ingredient may be contained in microcapsules to control the rate of loss from a surface or an article; a precursor molecule, which slowly disintegrates on a surface or in an article, may be used to control the rate of release the repellent active ingredient; or a synergist may be used to continually stimulate the evaporation of the repellent active ingredient from the composition.

The release of the repellent active ingredient may be accomplished, for example, by sub-micron encapsulation, in which the active ingredient is encapsulated (surrounded) within a surface nourishing protein just the way air is captured within a balloon. The protein may be used, for example, at about a 20% concentration. A dose contains many of these protein capsules that are suspended in either a water-based lotion, or water for spray application. After contact with skin or other surface, the protein capsules begin to breakdown releasing the encapsulated repellent active ingredient. The process continues as each microscopic capsule is depleted then replaced in succession by a new capsule that contacts the skin or other surface and releases its repellent active ingredient. The process may take up to 24 hours for one application. Because a protein adheres very effectively to a surface such as skin, these formulations are very resistant to perspiration (sweat-off) and water from other sources.

One of the distinct advantages of the repellent active ingredients as described above is that they are all characterized by a relative volatility that makes them suitable for use to obtain a desirably high level of concentration of a repellent active ingredient on, above and around a surface or article, as described above. One or more of these compounds are typically used for such purposes as a repellent active ingredient in a composition in which the compounds are admixed with a diluent or carrier suitable for wet or dry application of the composition to any surface in the form, for example, of a liquid, aerosol, gel, aerogel, foam or powder (such as a sprayable powder or a dusting powder). Suitable diluents or carriers include any one of a variety of commercially available organic and inorganic liquid, solid, or semi-solid diluents or carriers or formulations thereof usable in formulating skin or tick/insect repellent products. When formulating a skin product or topical tick/insect repellent, it is preferred to select a dermatologically acceptable diluent or carrier.

Desirable properties of a topical composition or article repellent to insects and/or arthropods include low toxicity, resistance to loss by water immersion or sweating, low or no odor or at least a pleasant odor, ease of application, and rapid formation of a dry tack-free surface film on the host's skin or other surface. In order to obtain these properties, the formulation for a topical repellent or repellant article should permit animals infested with insects and/or arthropods (e.g. dogs with fleas, poultry with lice, cows with horn flies or ticks, and humans) to be treated with a repellent active ingredient (including a composition thereof) by contacting the skin, hide, hair, fur or feathers or other surface of such human or animal with an effective amount of the repellent for repelling the insect or arthropod from the human or animal host.

The application of an effective amount of an repellent active ingredient on a surface subject to attack by insects (such as skin, hide, hair, fur, feathers or plant or crop surface) may be accomplished by dispersing the repellent active ingredient into the air or dispersing the repellent active ingredient as a liquid mist or incorporated into a powder or dust, and this will permit the repellent active ingredient to fall on the desired host surfaces. It may also be desirable to formulate a composition of a repellent active ingredient by combining it with a fugitive vehicle for application in the form of a spray. Such a composition may be an aerosol, sprayable liquid or sprayable powder composition adapted to disperse the repellent active ingredient into the atmosphere by means of a compressed gas, or a mechanical pump spray. Likewise, directly spreading of a liquid/semi-solid/solid composition on the host in wet or dry form (as a friable solid, for example) is an effective method of contacting a surface of the host with an effective amount of the repellent active ingredient.

Further, it may also be desirable to combine one or more of the repellent active ingredients described herein with one or more other compounds known to have insect repellency in a composition to achieve the synergistic effect as may result from such a combination. Suitable compounds known for insect repellency combinable for such purpose include but are not limited to one or more of the following: dihydronepetalactone, benzil, benzyl benzoate, 2,3,4,5-bis(butyl-2-ene) tetrahydrofurfural, butoxypolypropylene glycol, N-butylacetanilide, normal-butyl-6,6-dimethyl-5,6-dihydro-1,4-pyrone-2-carboxylate, dibutyl adipate, dibutyl phthalate, di-normal-butyl succinate, N,N-diethyl-meta-toluamide, dimethyl carbate, dimethyl phthalate, 2-ethyl-2-butyl-1,3-propanediol, 2-ethyl-1,3-hexanediol, di-normal-propyl isocinchomeronate, 2-phenylcyclohexanol, normal-propyl N,N-diethylsuccinamate, p-methane-3,8-diol, IR-3535 and picaridin.

In addition to one or more of the repellent active ingredients described herein, a tick/insect repellent composition may also include one or more essential oils and/or active ingredients of essential oils. "Essential oils" are defined as any class of volatile oils obtained from plants possessing the odor and other characteristic properties of the plant. Examples of useful essential oils include one or more of the following: almond bitter oil, anise oil, basil oil, bay oil, caraway oil, cardamom oil, cedar oil, celery oil, chamomile oil, cinnamon oil, citronella oil, clove oil, coriander oil, cumin oil, dill oil, eucalyptus oil, fennel oil, ginger oil, grapefruit oil, lemon oil, lime oil, mint oil, parsley oil, peppermint oil, pepper oil, rose oil, spearmint oil (menthol), sweet orange oil, thyme oil, turmeric oil, and oil of wintergreen. Examples of active ingredients in essential oils are: citronellal, methyl salicylate, ethyl salicylate, propyl salicylate, citronellol, safrole, and limonene.

The insects and arthropods that may be repelled by the compounds and/or compositions provided by this invention may include any member of a large group of invertebrate animals characterized, in the adult state (non-adult insect states include larva and pupa) by division of the body into head, thorax, and abdomen, three pairs of legs, and, often (but not always) two pairs of membranous wings. This definition therefore includes ticks and a variety of biting insects (e.g. ants, bees, chiggers, fleas, mosquitoes, wasps), biting flies [e.g. black flies, green head flies, stable flies, horn flies (haematobia irritans)], wood-boring insects (e.g. termites), noxious insects (e.g. houseflies, cockroaches, lice, roaches, wood lice), and household pests (e.g. flour and bean beetles, dust mites, moths, silverfish, weevils).

A host from which it may be desired to repel a tick or insect may include any plant or animal (including humans) affected by the tick or insect. Typically, hosts are considered to be tick/insect-acceptable food sources or tick/insect-acceptable habitats. For example, humans and animals serve as food source hosts for blood-feeding insects and arthropods such as biting flies, chiggers, fleas, mosquitoes, ticks and lice.

In another embodiment, a compound as described herein may be used as a fragrance compound or as an active in a fragrance composition, and be applied in a topical manner to human or animal skin or other surface to impart a pleasing fragrance, as in skin lotions and perfumes for humans or pets.

Particularly because of the pleasant aroma associated with the compounds described herein, a further embodiment of this invention is one in which one or more of those compounds are formulated into a composition for use as a product that is directed to other fundamental purposes. The fragrance of these products will be enhanced by the presence therein of one or more of the compounds having thus far been described herein only with reference to its value as a repellent active ingredient Such products include without limitation colognes, lotions, sprays, creams, gels, ointments, bath and shower gels, foam products (e.g. shaving foams), makeup, deodorants, shampoo, hair lacquers/hair rinses, and personal soap compositions (e.g. hand soaps and bath/shower soaps). The compound(s) may of course be incorporated into such products simply to impart a pleasing aroma, but an additional beneficial effect is that they will also possess tick/insect repellent qualities.

A corresponding aspect of the wide variety of products discussed above is a further alternative embodiment of this invention, which is a process for fabricating a composition of matter, a topical treatment for skin, or an article of manufacture, by providing as the composition, or incorporating into the composition, skin treatment or article, one or more the compounds described above. Such products, and the method and process described above, illustrate the use of these compounds as a fragrance compound or perfume, or in a fragrance composition or formulation, or in a topical treatment for skin, or in an article of manufacture. In fabricating a composition of matter, for example, the composition could be prepared as a sprayable liquid, an aerosol, a foam, a cream, an ointment, a gel, a paste, a powder or a friable solid. The process of fabrication in such case would thus include admixing an active ingredient with suitable diluents or carriers or other inert ingredients to facilitate delivery in the physical form as described, such as liquid carriers that are readily sprayed; a propellant for an aerosol or a foam; viscous carriers for a cream, an ointment, a gel or a paste; or dry or semi-solid carriers for a powder or a friable solid.

A composition containing one or more of the above described compounds as an active ingredient prepared as an insect/arthropod repellent, fragrance product, skin treatment or other personal care product may also contain other therapeutically or cosmetically active adjuvants or supplemental ingredients as are typical in the personal care industry. Examples of these include fungicides, sunscreening agents, sunblocking agents, vitamins, tanning agents, plant extracts, anti-inflammatory agents, anti-oxidants, radical scavenging agents, retinoids, alpha-hydroxy acids, antiseptics, antibiotics, antibacterial agents, antihistamines; adjuvants such as thickeners, buffering agents, chelating agents, preservatives, gelling agents, stabilizers, surfactants, emollients, coloring agents, aloe vera, waxes; and mixtures of any two or more thereof.

To make a composition suitable for use as described above, it is typically desirable to prepare a formulated composition of the repellent active ingredient and one or more components selected to serve a specific beneficial purpose in the composition. A description of those types of components, and examples of suitable choices for each component, are set forth below. Any mixing means known in the art may be used to prepare the formulated composition.

In this invention, a variety of diluents for the above-disclosed active ingredient compounds can be used. The diluent allows the formulation to be adjusted to an effective concentration of the active ingredient compound. When formulating a topical tick/insect repellent, the active ingredient compound(s) are preferably mixed in a dermatologically acceptable diluent. The diluent may further provide water repellency, prevent skin irritation, and/or soothe and condition skin. Factors to consider when selecting diluent(s) for any formulation of tick/insect repellent include commercial availability, cost, repellency, evaporation rate, odor and stability. The carrier, moreover, should preferably also be one that will not be harmful to the environment. Some carriers can themselves have repellent properties.

Examples of diluents suitable for use herein include water, and liquid aliphatic hydrocarbons (e.g., pentane, hexane, heptane, nonane, decane and their analogs) and liquid aromatic hydrocarbons. Examples of other liquid hydrocarbons include oils produced by the distillation of coal and the distillation of various types and grades of petrochemical stocks, including kerosene oils which are obtained by fractional distillation of petroleum. Other petroleum oils include those generally referred to as agricultural spray oils (e.g., the so-called light and medium spray oils, consisting of middle fractions in the distillation of petroleum and which are only slightly volatile). Such oils are usually highly refined and may contain only minute amounts of unsaturated compounds. Such oils, moreover, are generally paraffin oils and accordingly can be emulsified with water and an emulsifier, diluted to lower concentrations, and used as sprays. Tall oils, obtained from sulfate digestion of wood pulp, like the paraffin oils, can similarly be used. Other organic liquid diluents can include liquid terpene hydrocarbons and terpene alcohols such as alpha-pinene, dipentene, terpineol, and the like.

Still other suitable diluents include organic solvents such as aliphatic and aromatic alcohols, esters, aldehydes, and ketones. Aliphatic monohydric alcohols include methyl, ethyl, normal-propyl, isopropyl, normal-butyl, sec-butyl, and tert-butyl alcohols. Suitable alcohols include glycols (such as ethylene and propylene glycol) and pinacols. Suitable polyhydroxy alcohols include glycerol, arabitol, erythritol, sorbitol, and the like. Finally, suitable cyclic alcohols include cyclopentyl and cyclohexyl alcohols.

Conventional aromatic and aliphatic esters, aldehydes and ketones can be used as carriers, and occasionally are used in combination with the above-mentioned alcohols. Still other liquid carriers include relatively high-boiling petroleum products such as mineral oil and higher alcohols (such as cetyl alcohol).

Other carriers suitable for use in a composition of this invention, in addition to water or ethyl alcohol, include one or more of the following: acetone, methyl ethyl ketone, tetrahydrofuran, cyclohexane, a C6~C20 linear, branched or cyclic alkane, alkanol or alkane polyol, C6~C400 polyethylene glycols, C30~C150 polypropylene glycols, alkoxylated alcohols (such as the polyoxyethyene and/or polyoxypropylene ether of a C4~C60 alcohol; or an ester prepared as an amyl, benzyl, butyl, cetyl, decyl, ethyl, hexyl, methyl, octyl, propyl, acetate, adipate, benzoate, glutarate, laurate, maleate, myristate, oxalate, palmitate, phthalate, salicylate, sebacate, stearate or succinate.

Compositions as provided by this invention may also contain adjuvants or modifiers known in the art of personal care product formulations, such as thickeners, buffering agents, chelating agents, preservatives, fragrances, antioxidants, gelling agents, stabilizers, surfactants, emolients, coloring agents, aloe vera, waxes, other penetration enhancers and mixtures thereof, and therapeutically or cosmetically active agents.

Additionally, the compositions of the present invention may also contain other adjuvants or modifiers such as one or more therapeutically or cosmetically active ingredients. Exemplary therapeutic or cosmetically active ingredients useful in the compositions of the invention include fungicides, sunscreening agents, sunblocking agents, vitamins, tanning agents, plant extracts, anti-inflammatory agents, antioxidants, radical scavenging agents, retinoids, alpha-hydroxy acids, emollients, antiseptics, antibiotics, antibacterial agents or antihistamines, and may be present in an amount effective for achieving the therapeutic or cosmetic result desired.

Additionally, the compositions of this invention may contain one or more other adjuvants, modifiers or additives typical for use in the cosmetics industry such as an antioxidant, an emulsion stabilizer, a preservative, a propellant, an emollient, a sunscreen agent, a surfactant, an emulsifying agent, a solubilizing agent and/or an ultraviolet light absorber. Examples of materials that may function as such additives are set forth below.

The compositions of this invention may include one or more materials that may function as an antioxidant, such as reducing agents and free radical scavengers. Suitable materials that may function as an antioxidant include one or more of the following: acetyl cysteine, ascorbic acid, t-butyl hydroquinone, cysteine, diamylhydroquinone, erythorbic acid, ferulic acid, hydroquinone, p-hydroxyanisole, hydroxylamine sulfate, magnesium ascorbate, magnesium ascorbyl phosphate, octocrylene, phloroglucinol, potassium ascorbyl tocopheryl phosphate, potassium sulfite, rutin, sodium ascorbate, sodium sulfite, sodium thloglycolate, thiodiglycol, thiodiglycolamide, thioglycolic acid, thiosalicylic acid, tocopherol, tocopheryl acetate, tocopheryl linoleate, tris (nonylpheny)phosphite.

The compositions of this invention may also include one or more materials that may function as an emulsion stabilizer. These materials would not act as primary emulsifiers, but would prevent or reduce the coalescence of emulsified droplets. This could be accomplished, for example, by modifying the continuous or the disperse phase of the emulsion through electrical repulsion, from changes in viscosity, or from film formation on the droplet surface. Suitable materials that may function as an emulsion stabilizer include one or more of the following: $C_{15}$~$C_{18}$ glycols; $H(OCH_2CH_2)_nOH$ where n=350 to 160,000; $C_{10}$~$C_{50}$ alcohols such as cetyl, lauryl, myristyl, stearyl, tallow alcohol; $C_{10}$~$C_{50}$ linear, branched or cylic aliphatic or aromatic alcohols; aluminum behenate, caprylate, dilinoleate, dimyristate, distearate, isostearate, lanolate, laurate, myristate, palmitate, stearate, or tristearate; calcium carrageenan; calcium laurate, myristate or stearate; C18~C38 alkyl hydroxystearoyl stearate, carboxymethyl hydroxyethylcellulose, carboxymethyl hydroxypropyl guar, cellulose gum, cetyl hydroxyethylcellulose, cholesterol, glucose pentaacetate, glycol cetearate, glycol hydroxystearate, montanate, oleate, palmitate, ricinoleate or stearate; hydroxybutyl methytcellulose, hydroxyethylcellulose, hydroxyethyl ethylcellulose, hydroxypropylcellulose, hydroxypropyl guar, hydroxypropyl methylcellulose, methylcellulose, methyl hydroxyethylcellulose, microcrystalline cellulose, pectin, potassium alginate, potassium carrageenan, sodium carbomer, sodium carboxymethyl dextran, sodium carrageenan, sodium cellulose sulfate, sodium cyclodextrin sulfate, stearylvinyl ether/maleic anhydride ("MA") copolymer, styrene/MA copolymer, polyvinyl acetate, and xanthan gum.

The compositions of this invention may also include one or more materials that may function as a preservative, which would prevent or retard microbial growth and thus protect the composition (or products made therefrom) from spoilage or from inadvertent contamination by the consumer during use. Suitable materials that may function as a preservative include one or more of the following:

Ammonium Benzoate or Propionate
Isobutylparaben
Isodecylparaben
Benzoic Acid
Isopropyl Cresol, Paraben or Sorbate
Benzotriazole
Magnesium Benzoate
Benzylparaben
Magnesium Propionate
Magnesium Salicylale
Butyl Benzoate
Dimethyl Hydroxymethyl Pyrazole
Butylparaben
Dimethylol Ethylene Thiourea
Calcium Benzoate, Salicylate, Sorbate, Paraben or Propionate
Dimethyl Oxazolidine
Methyl Hydroxyl Hydantoin
Methyldibromo Glutaronitrile
Methylisothiazolinone
Methyl, ethyl, propyl or phenyl paraben
Chlorhexidine Diacetate, Digluconate or Dihydrochloride
Glutaral
Glyoxal
Chloroacetamide
Hexamidine
Chlorobutanol
Hexamidine Diparaben
Phenol
Hexamidine Paraben
Octyl, Lauryl, Myristyl, Palmitoyl or Stearyl Salicylate
Octyl, Lauryl, Myristyl, Palmitoyl or Stearyl Benzoate Chlorophene
4Hydroxybenzoic Acid
Phenoxyethylparaben
P-Chlorophenol
Phenoxyisopropanol
Chlorothymol
Phenyl Benzoate
Potassium Salicylate, Sorbate, Benzoate, Propylparaben, Butylparaben, Ethylparaben, Methylparaben, Paraben, Phenoxide, o-Phenylphenate or Propionate
Propionic Acid
Propyl Benzoate
Silver Borosilicate
Silver Magnesium Aluminum Phosphate
Sorbic Acid
Sodium Hydroxymethylglycinate, Methylparaben, Paraben, Phenolsulfonate, Phenoxide, o-Phenylphenate, Propionate, Propylparaben, Pyrithione, Salicylate, Sorbate, Benzoate, Butylparaben, p-Chloro-m-Cresol, Dehydroacetate, Ethylparaben, Formate or Hydroxymethane Sulfonate
Zinc Pyrithione The compositions of this invention may also include one or more materials that may function as a propellant, which are chemicals used for expelling products from pressurized containers (aerosols). The functionality of a propellant depends on its vapor pressure at ambient temperature and its compressibility. Liquids or gases can be used as propellants as long as the pressure developed within the container is safely below the container's bursting pressure under normal storage and use conditions. Suitable materials that may function as a propellant include one or more of the following: nitrogen, carbon dioxide, $CH_3CF_2$, $CH_3CClF_2$, $CH_3CHF_2$, nitrous oxide, dimethyl ether, butane, isobutene, pentane, ethane, isopentane, and propane.

The compositions of this invention may also include one or more materials that may function as an emollient, which is a cosmetic ingredient that maintains the soft, smooth, and pliable appearance of skin. The purpose of an emollient is to remain on the skin surface or in the stratum corneum to act as a lubricant, to reduce flaking, and to improve the skin's appearance. These are predominantly hydrophobic materials that are from the class of chemicals described as hydrocarbons (e.g. mineral oil, polyisobutene and polyalphaolephins); esters (e.g. isopropyl palmitate, octyl palmitate and $C12~C15$ alkyl benzoate); triglycerides (e.g. caprylic/capric triglyceride, and vegetable oils such as sesame oil); polypropylene/polyethylene oxide polymers; and silicones such as dimerthylpolysiloxanes, cyclopentasiloxane and phenyl trimethicone. Suitable materials that may also function as an emollient include one or more of the following:

Acetylated Lanolin or Lanolin Alcohol
Bisphenylhexamethicone
Caprylic/Capric Glycerides
Caprylic/Capric/Succinic Triglyceride
Acetylated Sucrose Distearate
Acetyl Trihexyl Citrate
Butyl Isostearate, Myristate, Oleate or Stearate
Caprylyl Glycol
Acetyl Trioctyl Citrate
Cetearyl Octanoate or Palmitate
*Prunus* Armenlaca Kernel Oil
Cetyl Acetate, Caprylate, Lactate, Laurate, Octanoate or Oleate
$C14~C15$ Alcohols
$C_4~C_{20}$ linear or branched aliphatic esters of $C_{10}~C_{30}$ carboxylic acids
Argania Spinosa Oil
$C12~C28$ Alkyl Acetate, Benzoate or Lactate or Octanoate
*Persea* Gratissima Oil
$C24~C28$ Alkyl Methicone
$C12~C13$ Alkyl Octanoate
Cetyl Glycol, Glycol Isostearate or Glycol Palmitate
Benzyl Laurate
Isostearyl, Myristyl, Lauryl, Isocetyl, Pentadecyl, Oleyl, Tridecyl or Undecyl Alcohol
Isostearyl Glyceryl Ether
Isostearyl Benzoate, Lactate, Neopentanoate, Octanoate, Palmitate or Myristate
Rosa Moschata Seed Oil
Isoamyl Laurate
Isobutyl Myristate, Palmitate, Pelargonate or Stearate
Isopropyl Laurate, Myristate, Palmitate or Stearate
Myristyl Isostearate, Lactate, Neopentanoate, Octanoate or Propionate
*Actinidia Chinensis* Seed Oil
Isocetyl Isodecanoate, Palmitate or Stearate
Lanolin, Lanolin Oil or Lanolin Wax
Isodecyl Citrate, Hydroxystearate, Laurate, Myristate, Neopentanoate, Palmitate or Stearate
Nonyl Acetate
Lauryl Glycol
Lauryl Isostearate or Lactate
Octyldecanol or Octyldodecanol
Octyl, Lauryl, Myristyl, Palmitoyl or Stearyl Benzoate
Isohexadecane
Isohexyl Neopentanoate, Palmitate or Laurate
Octyl Hydroxystearate, Laurate, Isopalmitate, Isostearate, Myristate, Neopentanoate, Oleate, Palmitate or Stearate
Isopropyl Hydroxycetyl Ether
Isopropyl Hydroxystearate, Isostearate, Lanolate, Laurate, Linoleate, Myristate or Oleate
Oleyl Acetate, Lactate or Oleate
Methyl Hydroxystearate, Laurate, Isostearate, Myristate, Oleate, Palmitate or Pelargonate
Isopropyl Palmitate, Isopropyl or Stearate
Isosorbide Laurate
*Passiflora* Eduls Oil
Polyethyelene Glycol Glycerides
Polyglyceryl Oleyl Ether
Polyethylene Glycol Castor Oil
Pentaerythrityl Dioleate, Distearate, Stearate, Tetrabenzoate or Trioleate
Propylene Glycol Hydroxystearate Stearate, Laurate, Linoleate, Myristate, Ricinoleate, Stearte, Oleate, Soyate or Caprylate
Propylene Glycol Myristyl Ether or Myristyl Ether Acetate
Polypropylene Glycol Lauryl, Cetyl, Stearyl, Oleyl or Pentaerythrityl Ether
Stearyl Acetate, Benzoate or Lactate
Stearyl Glycol Isostearate or Citrate
Polypropylene Glycol/Polyethylene Glycol
Trimethylolpropane or Propene
Tris(Tributoxysiloxy)Methylsilane.

The compositions of this invention may also include one or more materials that may function as as a sunscreen agent. Under 58 Fed. Reg. 28194 (May 12, 1993), a sunscreen active ingredient is defined as an "ingredient that absorbs at least 85 percent of the radiation in the UV range at wavelengths from 290 to 320 nanometers, but may or may not transmit radiation at wavelengths longer than 320 nanometers." Suitable materials that may function as a sunscreen agent include one or more of the following: aminobenzoic acid ("PABA"), glyceryl aminobenzoate (Glyceryl PABA), oxybenzone (benzophenone-3), cinoxate, homosalate, octyl dimethyl PABA, diethanolamine methoxycinnamate, 2-ethylhexyl; lauryl, myristyl, palmitoyl, or stearyl 4-methoxycinnamate; phenylbenzimidazole sulfonic acid, menthyl anthranilate, digalloyl trioleate, octocrylene, sulisobenzone (benzophenone-4), dioxybenzone (benzophenone-8), octyl methoxycinnamate, titanium dioxide, ethyl 4-[bis(hydroxypropyl)] aminobenzoate (ethyl dihydroxypropyl PABA), octyl salicylate, and trolamine salicylate.

The compositions of this invention may also include one or more materials that may function as as an emulsifying agent, and/or also as a surfactant or a solubilizing agent. Such a material may be used to reduce surface tension, to form complex films on the surface of emulsified droplets, to create a repulsive barrier on emulsified droplets to prevent their coalescence, to retard physical changes in emulsions during shelf-life or to cause a solute to become part of a micelle formed by a surfactant.

Emulsifying agents suitable for use herein include anionic emulsifiers that have a hydrophobic and hydrophilic moiety in which the hydrophobic (lipophilic) moiety has a negative charge. These types of emulsifiers are generally:
  fatty acid soaps where the hydrophobic portion is generally composed of an organic acid with a carbon chain from C8~C20, and the hydrophilic potion is generally composed of sodium, potassium, triethanolamine, or aminomethylpropanol, e.g. triethanolamine stearate or sodium stearate;
  phosphates and sulfates where the hydrophobic portion is generally composed of an organic alcohol with a C8~C20 carbon chain, and the hydrophilic portion is generally composed of a phosphate or a sulfate derived from phosphoric acid or sulfuric acid, and neutralized with an alkali, e.g. diethanol amine cetyl phosphate or sodium lauryl sulfate.

Emulsifying agents suitable for use herein also include non-ionic emulsifiers that have a hydrophobic and hydrophilic moiety in which the hydrophobic (lipophilic) moiety is usually a fatty acid (or difatty acid), a fatty alcohol, a polypropylene glycol, a C6~C20 alcohol, or a silicone (e.g. dimethyl polysiloxane). Typical non-ionic emulsifiers include: fatty esters in which the hydrophilic portion is a polyethylene glycol in which the number of ethylene glycol groups can be 2~150 (n=2-150), and can form an ester with an acid such as lauric or stearic acid.
  fatty ethers in which the hydrophilic portion is a polyoxyethylene in which the number of ethylene oxide groups can be 2~150, and can be formed from an alcohol such as lauryl or stearyl alcohol.
  block copolymers such as those derived from reacting polyethylene oxide (POE) and polypropylene oxide (PPO).

Emulsifying agents suitable for use herein also include cationic emulsifiers that have a hydrophobic and hydrophilic moiety in which the hydrophobic (lipophilic) moiety has a net positive charge coming from a "quaternized" nitrogen group. The quaternized ammonium group can have as its anion a chloride, ethosulfate or methosulfate. The hydrophobic group can be a mono, di or tri fatty group from the group of fatty alcohols and fatty acids having a C8~C22 carbon chain or a silicone oil, e.g. behentrimonium chloride.

Suitable materials for use herein as an emulsifying agent also include one or more of the following:
  C6~C400 polyethylene glcycols,
  C30~C150 polypropylene glycols,
  alkoxylated alcohols (such as the polyoxyethyene and/or polyoxypropylene ether of a C4~C60 alcohol;
  C50~C650 linear or branched dihydroxy polyoxyethylene/polyoxypropylene block copolymers
  C50~C650 branched polyhydroxy polyoxyethylene/polyoxypropylene block copolymers of ethylene diamine
  C12~C330 ethoxylated alkyl phenols
  C16~C140 polyethylene glycol ether of C12~C60 alcohols
  Carboxylic acid esters of C12~C330 ethoxylated alkyl phenol
  Esters of C12~C40 Carboxlic Acid and C8~C40 Polyethylene Glycol
  Esters of Caprylic or Capric Triglyceride and C8~C40 Polyethylene Glycol
  Phosphoric acid esters of C12~C330 ethoxylated alkyl phenol
  Phosphoric acid esters and diesters of C16~C140 polyethylene glycol ether of C12~C60 alcohols
  Abietic Acid
  Calcium Stearoyl Lactylate
  Cetethyl Morpholinium Ethosutfate
  Cetrimonium Bromide, Chloride, Methosulfate or Tosylate
  Cetyl Alcohol
  Cetyl Dimethicone Copolyol
  Cetyl Glyceryl Ether/Glycerin Copolymer
  Cetyl Phosphate
  Cetearyl Glucoside
  Dextrin Behenate, Laurate, Myristate, Palmitate or Stearate
  Dicetyl Phosphate
  Diethytaminoethyl Laurate or Stearate
  Dimethyl Octynediol
  Dimyristyl Phosphate
  Glyceryl Arachidate, Behenate, Caprylate, Caprate, Cocoate, Erucate, Hydrogenated Rosinate, Hydroxystearate, Isopalmitate, Isostearate, Isotridecanoate/Stearate/Adipate, Lanolate, Laurate, Oleate, Linoleate, Linolenate, Oleate, Montanate, Myristate, Palmitate, Stearate, Palmitoleate, Ricinoleate or Uridecylenate
  Glycol Octanoate
  Hydrogenated Lecithin
  Hydrogenated Palm Glyceride
  Hydroxycetyl Phosphate
  Hydroxyethyl Glyceryl Oleate and/or Stearate
  Lanolin
  Laurtrimonium Chloride
  Lauryl Phosphate
  Lecithin
  Mannitan Laurate or Oleate
  Myristoyl Methylalanine
  Palmitic Acid
  Octoxyglyceryl Behenate or Palmitate
  Pelargonic Acid
  Pentaerythrityl Stearate
  Phosphatidylcholine
  Potassium Laurate, Myristate, Oleate, Lauryl Hydroxypropyl Sulfonate, Cetyl Phosphate, Lauryl Sulfate, Palmate, Palmitate, Ricinoleate or Stearate
  Sodium Palmate, Palmitate, Phthalate Stearyl Amide, Ricinoleate, Stearate, Stearyl Sulfate, Trideceth Sulfate, Tridecyl Sulfate, Undecylenate, Lauroyl Lactylate, Lauryl Phosphate, Myristate, Oleate, Oleoyl Lactylate, Behenoyl Lactylate, Caproyl Lactylate, Caprylate, Isostearoyl Lactylate or Laurate
  Propylene Glycol Behenate, Caprylate, Hydroxystearate, Isostearate, Laurate, Linoleate, Unolenate, Myristate, Oleate, Ricinoleate or Stearate Sorbitan Caprylate, Diisostearate, Dioleate, Distearate, Isostearate, Laurate, Oleate, Palmitate, Sesquiisostearate, Sesquioleate, Sesquistearate, Stearate, Triisostearate, Trioleate or Tristearate
Raffinose Oleate
Stearic Acid
Stearoyl Lactylic Acid
Stearyl Alcohol
Sucrose Dilaurate, Distearate, Laurate, Myristate, Oleate, Palmitate, Polylaurate, Polylinoleate, Polyoleate, Polypalmate or Polystearate
C32~C82 polyethylene glycol ethers of behenyl alcohol
C20~C106 polyethylene glycol ethers of cetyl alcohol
C28~C80 polyethylene glycol ethers of cetyl or oleyl alcohol
C20~C70 polyethylene glycol ethers of cetyl and/or stearyl alcohol
C20~C80 polyethylene glycol ethers of cholesterol
C16C24 polyethylene glycol ethers of decyl alcohol
C40~C80 polyethylene glycol ethers of dihydrocholesterol
C20~C60 polyethylene glycol ethers of isocetyl alcohol
C18~C30 polyethylene glycol ethers of isodecyl alcohol
C18~C40 polyethylene glycol ethers of isolauryl alcohol
C20~C120 polyethylene glycol ethers of isostearyl alcohol
C12~C120 polyethylene glycol ethers of glyceril caprate, caprylate, laurate, myristate, oleate, palmitate or stearate
C14~C100 polyethylene glycol ethers of lauryl alcohol
C16~C24 polyethylene glycol ethers of myristyl alcohol
C20~C70 polyethylene glycol ethers of oleyl alcohol
C10~C100 polyethylene/polypropylene glycol ethers of butyl alcohol
C20~C106 polyethylene/polypropylene glycol ethers of cetyl alcohol
C20~C100 polyethylene/polypropylene glycol ethers of decyl alcohol
C14~C100 polyethylene/polypropylene glycol ethers of lauryl alcohol
Carboxylic acid ester of C20~C120 polyethylene glycol ethers of isostearyl alcohol
Carboxylic acid esters of C14~C100 polyethylene glycol ethers of lauryl alcohol
Carboxylic acid esters of C16~C24 polyethylene glycol ether of myristyl alcohol
Citric acid diesters of C14~C100 polyethylene glycol ether of lauryl alcohol
Isopropyl Laurate, Myristate, Palmitate or Stearate
Lauric acid esters of C30~C120 polyethylene glycol ether of sorbitol
Octyl, Lauryl, Myristyl, Palmitoyl or Stearyl Salicylate
Phosphoric acid esters of C20~C106 polyethylene glycol ether of cetyl alcohol
Phosphoric acid esters of C20~C120 polyethylene glycol ether of isostearyl alcohol
Phosphoric acid diesters of C14~C100 polyethylene glycol ether of lauryl alcohol
Phosphoric acid esters and/or diesters of C20~C70 polyethylene glycol ether of oleyl alcohol
Stearic acid ester of C15~C30 polyethylene glycol ethers of glycerin
Stearic acid ester of C20~C60 polyethylene glycol ethers of isocetyl alcohol
Stearic acid ester of C20~C120 polyethylene glycol ethers of isostearyl alcohol
Diethanolamine salt of phosphoric acid ester of C20~C106 polyethylene glycol ethers of cetyl alcohol
Diethanolamine salt of phosphoric acid ester of C20~C70 polyethylene glycol ethers of cetyl and/or stearyl alcohol
Diethanolamine salt of Phosphoric acid ester of C20~C70 polyethylene glycol ethers of oleyl alcohol
Disodium salt of citric acid ester of C14~C100 polyethylene glycol ethers of lauryl alcohol
Disodium salt of phosphoric acid ester of C14~C100 polyethylene glycol ethers of lauryl alcohol
Disodium salt of phosphoric acid ester of C20~C70 polyethylene glycol ethers of oleyl alcohol
Monoethanolamine salt of phosphoric acid ester of C20~C70 polyethylene glycol ethers of cetyl and/or stearyl alcohol
C12~C120 polyethylene glycol diesters of behenic, capric, caprylic, lauric, oleic, octanoic, palmitic or stearic acid
Polyesters of C6~C40 polyglycerin and behenic, capric, caprylic, lauric, oleic, octanoic, palmitic or stearic acid.

The compositions of this invention may also include one or more materials that may function as an ultravilolet light absorber to protect a product made from the composition from chemical or physical deterioration induced by ultraviolet light. UV absorbers, like sunscreen agents, have the ability to convert incident ultraviolet radiation into less damaging infrared radiation (heat). Suitable materials that may function as an ultraviolet light absorber include one or more of the following:

3-Benzylidene Camphor
Stilbenedisulfonate
Allantoin PABA
Benzalphthalide
Sulfonamide
Benzophenone
Benzylidene Camphor Sulfonic Acid
Ethyl Dihydroxypropyl PABA
Benzophenone substituted with one or more groups selected from hydroxyl, alkoxy, alkyl, halogen and sulfonate
Benzyl Salicylate
Bumetrizole
Ethyl PABA
Butyl Methoxydibenzoylmethane
Butyl PABA
Cinoxate
Ferulic Acid
Glyceryl Octanoate Dimethoxycinnamate
Di-t-Butyl Hydroxybenzylidene Camphor
Glyceryl PABA
Glycol Salicylate
Diisopropyl Methyl Cinnamate
Isoamyl p-Methoxycinnamate
Isopropylbenzyl Salicylate
Isopropyl Dibenzoylmethane
Octyl Triazone
Isopropyl Methoxycinnamate
PABA (aminobenzoic acid)
Menthyl Anthranilate or Salicylate
Pentyl Dimethyl PABA
Terephthaylidene Dicamphor Sulfonic Acid
4-Methylbenzylidene Camphor
Phenylbenzimidazole Sulfonic Acid
Titanium Dioxide
Octocrylene
TriPABA Panthenol
Octrizole
Potassium Methoxycinnamate
Urocanic Acid Octyl Dimethyl PABA
Potassium Phenylbenzimidazole Sulfonate
Octyl Methoxycinnamate or Salicylate
Sodium Phenylbenzimidazole Sulfonate The compositions of this invention may also include one or more materials that may function as a chelating agent to complex with metallic ions. This action will help to inactivate the metallic ions for the purpose of preventing their adverse effects on the stability or appearance of a formulated composition. Chelating agents suitable for use in a composition of this invention include one or more of the following: aminotrimethylene phosphonic acid, beta-alanine diacetic acid, calcium disodium EDTA, citric acid, cyclodextrin, cyclohexanediamine tetraacetic acid, diammonium citrate, diammonium EDTA, dipotassium EDTA, disodium azacycloheptane diphosphonate, disodium EDTA, disodium pyrophosphate, EDTA (ethylene diamine tetra acetic acid), gluconic acid, HEDTA (hydroxyethyl ethylene diamine triacetic acid), methyl cyclodextrin, pentapotassium triphosphate, pentasodium aminotrimethylene phosphonate, pentasodium triphosphate, pentetic acid, phytic acid, potassium citrate, potassium gluconate, sodium citrate, sodium diethylenetriamine pentamethylene phosphonate, sodium dihydroxyethylglycinate, sodium gluconate, sodium metaphosphate, sodium metasilicate, sodium phytate, triethanolamine ("TEA")-EDTA, TEA-polyphosphate, tetrahydroxypropyl ethylenediamine, tetrapotassium pyrophosphate, tetrasodium EDTA, tetrasodium pyrophosphate, tripotassium EDTA, trisodium EDTA, trisodium HEDTA, and trisodium phosphate.

The compositions of this invention may also include one or more materials that may function as a biocide. A biocide is utilized to inhibit the growth of, or destroy microorganisms, such as bacteria, fungi or yeast, and provide disinfectant. Biocides suitable for use in a composition of this invention include one or more of the following:

Aluminum Phenolsulfonate
Ammonium Phenolsulfonate
Benzalkonium Bromide or Chloride
Benzoxiquine
Bispyrithione
Boric Acid
Camphor Benzalkonium Methosulfate
Cetalkonium Chloride
Cetethyldimonium Bromide
Cetrimonium Bromide, Chloride, Methosulfate, Saccharinate, or Tosylate
Cetylpyridinium Chloride
Chlorhexidine
Chlorhexidine Diacetate
Chlorhexidine Digluconate
Chlorhexidine Dihydrochloride
p-Chloro-m-Cresol
Chlorophene
p-Chlorophenol
Chlorothymol
Chloroxylenol
Coal Tar
Colloidal Sulfur
Dequalinium Acetate
Dequalinium Chloride
Dichlorobenzyl Alcohol
Dichlorophene
Dichloro-m-Xylenol
Diiodomethyltolylsulfone
Dimethylol Ethylene Thiourea
Diphenylmethyl Piperazinylbenzimidazole
Sulfosuccinyl undecylenate
Domiphen Bromide
7-Ethylbicyclooxazolidine
Formaldehyde
Glutaral
Hexachlorophene
Hexamidine
Hexamidine Diisothionate, Diparaben, or Paraben
Hexetidine
Hydrogen Peroxide
Hydroxymethyl Dioxoazabicyclooctane
Isopropyl Cresols
Lauralkonium Bromide or Chloride
Laurtrimonium Bromide or Chloride
Laurylpyridinium Chloride
Mercuric Oxide
Methenammonium Chloride
Methylbenzethonium Chloride
Nonoxynol-9 Iodine
Nonoxynol-12 Iodine
Olealkonium Chloride
Oxyquinoline
Oxyquinoline Benzoate
Oxyquinoline Sulfate
Phenol
o-Phenylphenol
Phenyl Salicylate
Potassium Phenoxide
Potassium o-Phenylphenate
Potassium Salicylate
Potassium Troclosene
Propionic Acid
Sodium Phenolsulfonate
Sodium Phenoxide
Sodium o-Phenylphenate
Thiabendazole
2,2'-Thiobis(4-Chlorophenol)
Thiram
Triacetin
Triclocarban
Triclosan
Trioctyldodecyl Borate
Undecylenic Acid
Zinc Acetate
Zinc Aspartate The compositions of this invention may also include one or more materials that may function as a film former to foster the production, upon drying, of a continuous film on the surface to which a composition is applied. Film formers suitable for use in a composition of this invention include one or more of the following: albumen, ammonium alginate, balsam canada (abies balsamea), balsam peru (myroxylon pereirae), balsam tolu (myroxylon balsamum), benzoin (styrax benzoin) gum, butoxychitosan, butylated polyoxymethylene urea, calcium carrageenan, carboxymethyl chitosan, carboxymethyl dextran, carboxymethyl hydroxyethylcellulose, cellulose acetate, cellulose acetate butyrate, cellulose gum, chitosan, chitosan adipate, chitosan lactate, collodion, ethylcellulose, hydroxybutyl methylcellulose, hydroxyethylcellulose, hydroxypropyl chitosan, hydroxypropyl guar, maltodextrin, nitrocellulose, polybeta-alanine, serum albumin, shellac, sodium carbomer, sodium carboxymethyl chitin, sodium carrageenan, and zein; and polymers and copolymers containing monomeric units derived from compounds having, or providing as a result of the polymerization, one or more of the following functionalities: acrylamide, (meth)acrylate, vinyl pyrrolidone,(meth)acrylic acid, adipic acid, maleic anhydride, neopentyl glycol, trimellitic anhydride, diethylene glycol, diethylenetriamine, fumaric acid, phthalic acid, isophthalic acid, allyl stearate, vinyl acetate, styrene, aminomethyl propanol, benzoic acid, phthalic anhydride, pentaerythritol, butadiene, acrylonitrile, ethylene, epichlorohydrin, piperazine, cetearyl alcohol, vinyl alcohol, vinyl acetate, propylene, isobutylene, sodium maleate, octadecene, phthalic anhydride, benzoic acid, trimethylolpropane, butylene terephthalate, ethylene terephthalate, ethylglutamate, isobutene, methylene oxide, melamine, pentene, vinyl butyral, vinyl imidazolinium acetate, vinyl laurate, vinyl methyl ether, vinyl stearyl ether, itaconic acid, sodium acrylate, maleic acid, allyl ether, vinyl ether, allyl benzoate, benzyl phthalate, and butyl maleate;

The compositions of this invention may also include one or more materials that may function as a thixotropic agent to thicken the aqueous portions of a composition as provided hereby. The ability of the thixotropic agent to perform this function involves its water solubility, or hydrophilic nature. The predominant thixotropic agents can be from a variety of chemical types: natural thickeners based on xanthan, cellulose, carrageen, or guar; or synthetic materials such as polymers based, for example, on carboxyvinyl compounds (e.g. carbomers), acrylic acid, acrylates or acrylamides. Thixotropic agents suitable for use in a composition of this invention also include one or more of the following:

*Acacia* Famesiana
Acetamide monoethanol amine ("MEA")
Acrylic acid, acrylamide, acrylonitrogen and/or acrylate polymers and copolymers
Agar
Algin
Alginic Acid
Aluminum/Magnesium Hydroxide Stearate
Ammonium Alginate, Chloride, or Sulfate
Amylopectin
Arachidyl Alcohol
Arachidyl Glycol
Attapulgite
Behenamide diethanol amine ("DEA")
Behenamide MEA
Behenamidopropyl Betaine
Behenyl Betaine
Bentonite
Butoxy Chitosan
Calcium Alginate, Carrageenan, or Chloride
C20~C40 Alkyl Stearates
C6~C400 polyethylene glcycols
Capramide DEA
Carboxymethyl Chitin
Carboxymethyl Chitosan
Carboxymethyl Dextran
Carboxymethyl Hydroxyethylcellulose
Carnitine
Carrageenan (*Chondrus Crispus*)
Cellulose Gum
Cetearyl Alcohol
Cetyl Alcohol
Cetyl Betaine
Cetyl Glycol
Cetyl Hydroxyethylcellulose
Coco-Betaine
Coco-Hydroxysultaine
Coconut Alcohol
Coco/Oleamidopropyl Betaine
Decyl Alcohol
Decyl Betaine
Dextrin
Dibenzylidene Sorbitol
Erucamidopropyl Hydroxysultaine
Gelatin
Gellan Gum
Glyceryl Alginate
Guar (Cyanopsis TetragonolOba) Gum
Guar Hydroxypropyltrimonium Chloride
Hyaluronic Acid
Hydrated Silica
Hydrogenated Tallow
Hydroxy alkyl cellulose
Hydroxypropyl Chitosan
Hydroxypropyl Guar
Hydroxystearamide MEA
Isobutylene/Sodium Maleate Copolymer
Isostearamide DEA, MEA, or monoisopropanol amine ("MIPA")
Kelp
Lactamide MEA
Lanolinamide DEA
Lauramide DEA
Lauramide MEA
Lauramide/Myristamide DEA
Lauramidopropyl Betaine
Lauryl Alcohol, Betaine, Hydroxysultaine, or Sultaine
Lecithinamide DEA
Linoleamide DEA, MEA, or MIPA
Lithium Magnesium Silicate
Magnesium Aluminum Silicate
Magnesium Silicate
Methylcellulose
Methyl Hydroxyethylcellulose
Montmorillonite
Myristamide DEA, MEA, or MIPA
Myristamidopropyl Betaine
Myristyl Alcohol
Myristyl Betaine
Oat (*Avena* Sativa) Flour
Oat (*Avena* Sativa) Starch
Oleamide DEA, MEA, or MIPA
Oleamidopropyl Betaine
Oleyl Betaine
Palmamide DEA, MEA, or MIPA
Palmitamide DEA
Palmitamide MEA
Palmitamidopropyl Betaine
Palm Kernel Alcohol
Palm Kernelamide DEA, MEA, or MIPA
Palm Kernelamidopropyl Betaine
Peanut (*Arachis* Hypogaea) Flour
Pectin
Polycyclopentadiene
Polymethacrylic Acid
Polyvinyl Alcohol
Potassium Alginate
Potassium Carrageenan
Potassium Chloride
Potassium Palmate
Potssium Polyacrylate
Potassium Sulfate
Potato (*Solanum* Tuberosum) Starch
Propylene Glycol Alginate
Ricinoleamide DEA, MEA, or MIPA
Ricinoleamidopropyl Betaine
Sodium (Meth)Acrylate Copolymer
Sodium Carbomer
Sodium Carboxymethyl Chitin Sodium Carboxymethyl Dextran
Sodium Carrageenan
Sodium Cellulose Sulfate
Sodium Chloride
Sodium Cyclodextrin Sulfate
Sodium Isooctylene/maleic anhydride Copolymer
Sodium Magnesium Fluorosilicate
Sodium Oleate
Sodium Palmitate
Sodium Polystyrene Sulfonate
Sodium Silicoaluminate
Sodium Stearate
Sodium Sulfate
Soyamide DEA
Soyamidopropyl Betaine
Stearamide aminomethyl propanol ("AMP"), DEA, diisobutyl amine ("DIBA"), MEA, or MIPA
Stearamidopropyl Betaine
Stearyl Alcohol
Stearyl Betaine
Tallamide DEA
Tallow Alcohol
Tallowamide DEA
Tallowamide MEA
Tallowamidopropyl Betaine
Tallowamine Oxide
Tallow Betaine
TEA-Hydrochloride
Tragacanth (Astragalus Gummifer) Gum
Tridecyl Alcohol
Trimethylamine Magnesium Aluminum Silicate
Undecyl Alcohol
Undecylenamide DEA, or MEA
Wheat (*Triticum* Vulgare) Flour
Wheat (*Triticum* Vulgare) Starch
Xanthan Gum
Yeast Betaglucan
Yeast Polysaccharides.

The compositions of this invention may also include one or more materials that may function as a humectant. A humectant is added to a composition to retard moisture loss during use, which effect is accomplished, in general, by the presence therein of hygroscopic materials. Humectants suitable for use in a composition of this invention include one or more of the following: C6~C400 polyethylene glcycols, C6~C12 linear or branced aliphatic polyols, diglycerin, erythritol, fructose, glucose, glycerin, glycol, 1,2,6-hexanetriol, honey, hydrogenated honey, inositol, lactic acid, lactitol, maltitol, maltose, mannitol, polyglyceryl sorbitol, propylene glycol, sodium glucuronate, sorbitol, C6~C400 polyethylene glcycol ethers of sorbitol, sucrose, urea, urea-d-glucuronic acid, and xylitol.

The compositions of this invention may also include one or more materials that may function as a fragrance component impart a pleasant scent or aroma to the formulated composition. Fragrances suitable for use in a composition of this invention include one or more of the following:
Acetaldehyde
Acetyl Hexamethyl Tetralin
Amyl Benzoate, Cinnamal, or Salicylate
Anethole
Anise (Illicium Verum) Oil
p-Anisic Acid
Balm Mint (Melissa Officinalis) Oil
Basil (Ocimum Basilicum) Oil
Bayberry (Myrica Cerifera) Wax
Bay (Pimenta Acris) Oil
Bee Balm (Monarda Didyrna) Oil
Benzaldehyde
Benzoin (Styrax Benzoin) Gum
Benzyl Acetate, Alcohol, Benzoate, Cinnamate, or Salicylate
Bergamot (*Citrus Aurantium* Bergamia) 0l
Birch (*Betula* Alba) Oil
Bitter Almond (*Prunus* Amygdalus Amara) Oil
Bitter Orange (*Citrus Aurantium* Amara) Oil or Peel Extract
2-t-Butylcyclohexyl Acetate
2-t-Butylcyclohexyloxybutanol
Cabbage Rose (Rosa Centifolia) Oil
Cabbage Rose (Rosa Centifolia) Water
Calendula Officinalis Oil
Camphor
Camphylcyclohexanol
Caraway (Carum Carvi) Oil
Caryophyllane
Caryophyllene
Cardamon (Elettaria Cardamomum) Oil
Carvone
Cedarwood Oil
Cedrus Atlantica Oil
Chamomile (Anthemis Nobilis) Oil
Cinnamal
Cinnamon (*Cinnamomum Cassia*) Oil
Cinnamyl Acetate
Cinnamyl Alcohol
Citral
Citronella (Cymbopogon Nardus) Oil
Citronellal
Citronellol
Citronellyl Acetate
Clary (*Salvia* Sclarea) Oil
Clove (Eugenia Caryophyllus) Oil
Cloveleaf (Eugenia Caryophyllus) Oil
Coriander (Coriandrum Sativum) Oil
Coumarin
Cumin (Cuminum Cyminum) Extract
Cyclamen Aldehyde
Cypress (Cupressus Sempervirens) Oil
Dihydrocoumarin
Dihydrojasmonate
Dihydroxyindole
Dimethyl Brassylate
2,4-Dimethyl-3-Cyclohexene Carboxaldehyde
Dimethyl Hexahydronaphthyl Dihydroxymethyl Acetal
Dimethyloctahydro-2-Naphthaldehyde
2,6-Dimethyl-7-Octen-2-ol
Dipentene
Dog Rose (Rosa Canina) Hips Oil
Ethyl Benzoate
Ethyl Cyclohexyl Propionate
Ethyl Menthane Carboxamide
Ethyl Phenethyl Acetal
Ethyl Phenylacetate
Ethyl Vanillin
Eucalyptol
Eucalyptus Citriodora Oil
Eucalyptus Globulus Oil
Eugenol
Farnesol
Farnesyl Acetate
Fennel (Foeniculum Vulgare) Oil
Furfural
Galbanum (Ferula Galbaniflua) Oil
Gardenia Florida Oil
Geraniol
Geranium Maculatum Oil Geranyl Acetate
Ginger (Zingiber Officinale) Oil
Gluconolactone
Grapefruit (Citrus Grandis) Oil
Heliotropine
2-Heptylcyclopentanone
3-Hexenol
Humulane
Humulene
Hydroxycitronellal
Indigo Bush (Dalea Spinosa) Oil
Isoamyl Acetate
Isobutyl Methyl Tetrahydropyranol
Isopentylcyclohexanone
Isopropyl Benzoate
Isopropylphenylbutanal
Jasmine (Jasminum Officinale) Oil
*Juniperus* Communis Oil
*Juniperus Oxycedrus* Tar
*Juniperus Virginiana* Oil
Laurel (Laurus Nobilis) Oil
Lavandin (Lavandula Hybrida) Oil
Lavender (Lavandula Angustifolia) Oil
Lemon (*Citrus* Medica Limonum) Oil
Lemongrass (Cymbopogon Schoenanthus) Oil
Lesquerella Fendleri Oil
Lime (*Citrus* Aurantifolia) Oil
Linalyl Acetate
Linden (Tilia Cordata) Oil
Lovage (Levisticum Officinale) Oil
Mandarin Orange (*Citrus* Nobilis) Oil
Massoy Bark Oil
Matricaria (Chamomilla Recutita) Oil
p-Menthan-7-ol
Menthol
Menthoxypropanediol
Menthyl Acetate, Lactate, or Salicylate
Methoxyindane
p-Methyl Acetophenone
6-Methyl Coumarin
Methyl Diisopropyl Propionamide
Methyl 3-Methylresorcylate
Moroccan Chamomile Oil
Musk Ketone
Musk Rose (Rosa Moschata) Oil
Myrrh (*Commiphora* Myrrha)
Myrrh (*Commiphora* Myrrha) Oil
Myrtle (Myrtus Communis) Oil
Norway Spruce (*Picea* Excelsa) Oil
Nutmeg (Myristica Fragrans) Oil
Oakmoss (Evernia Prunastri) Extract
Olibanum
Olibanum (*Boswellia* Carterii) Extract
Olibanum (*Boswellia* Serrata) Extract
Orange (*Citrus Aurantium* Dulcis) Extract
Orange (*Citrus Aurantium* Dulcis) Flower Extract
Orange (*Citrus Aurantium* Dulcis) Flower Oil
Orange (*Citrus Aurantium* Dulcis) Flower Water
Orange (*Citrus Aurantium* Dulcis) Oil
Orange (*Citrus Aurantium* Dulcis) Peel Extract
Orris (Iris Florentina) Extract
Orris (Iris Pallida) Extract
Palmarosa (Cymbopogon Martini) Oil
Parsley (Carum *Petroselinum*) Seed Oil
Patchouli (Pogostemon Cablin) Oil
*Pelargonium* Graveolens Oil
Pennyroyal (Mentha Pulegium) Oil
Pentadecalactone
Peppermint (Mentha Piperita) Extract
Peppermint (Mentha Piperita) Oil
Phenethyl Acetate
Phenethyl Alcohol
Phenoxyethanol
Phenyl Benzoate
Pine (Pinus Palustris) Oil
Pine (Pinus Palustris) Tar Oil
Pistachio (Pistacia Vera) Nut Oil
Propyl Benzoate
Rosemary (Rosmarinus Officinalis) Oil
Rose Oil
Rosewood (Aniba Rosaedora) Oil
Sage (*Salvia Officinalis*) Oil
Sandalwood (Santalum Album) Oil
Sassafras Officinale Oil
Silver Fir (Abies Pectinata) Oil
Sweet Marjoram (Origanum Maiorana) Oil
Sweet Violet (*Viola Odorata*) Oil
Tea Tree (Melaleuca Alternifolia) Oil
Terpineol
Terpineol Acetate
Tetramethyl Cyclopentene Butenol
Thyme (Thymus Vulgaris) Oil
Thymol
Gamma-Undecalactone
Vanilla Planifolia
Vanilla Tahitensis
Vanillin
Vetiveria Zizanoides Oil
Yarrow (Achillea Millefolium) Oil
Ylang Ylang (Cananga Odorata) Oil.

In a further embodiment of this invention, a repellent active ingredient compound is incorporated into an article to produce an insect/arthropod repellent effect. Articles contemplated to fall within this embodiment include manufactured goods, including textile goods such as clothing, outdoor or military equipment as mosquito netting, natural products such as lumber, or the leaves of insect vulnerable plants.

In another embodiment of this invention, an active ingredient compound as described herein is incorporated into an article to produce a fragrance pleasing to humans, or is applied to the surface of an object to impart an odor thereto. The particular manner of application will depend upon the surface in question and the concentration required to impart the necessary intensity of odor. Articles contemplated to fall within these embodiments include manufactured goods, including textile goods, air fresheners, candles, various scented articles, fibers, sheets, paper, paint, ink, clay, wood, furniture (e.g. for patios and decks), carpets, sanitary goods, plastics, polymers, and the like. Tick/insect repellency may also be imparted to these articles by reason of the presence therein of an active ingredient compound as described herein.

A compound as described herein may be admixed in a composition with other components, such as desecribed above, in an amount that is effective for usage for a particular purpose, such as an insect/arthropod repellant, fragrance or other skin treatment. The amount of the active compound contained in a composition will generally not exceed about 80% by weight based on the weight of the final product, however, greater amounts may be utilized in certain applications, and this amount is not limiting. More preferably, a suitable amount of the compound will be at least about 0.001% by weight and preferably about 0.01% up to about 50% by weight; and more preferably, from about 0.01% to about 20% weight percent, based on the total weight of the total composition or article. Specific compositions will depend on the intended use.

A formulated mixture of one or more carriers, adjuvants and/or additives may be selected from the members of the groups thereof contained in the lists set forth above. They may also be selected from a subgroup of the members of the foregoing lists formed by omitting any one or more members from the whole groups as set forth in the above lists. As a result, a mixture of carriers, adjuvants and/or additives may in such instance not only be made from one or more members selected from any subgroup of any size that may be formed by all the various different combinations of individual members from the whole groups as set forth in the above lists, but may also be made in the absence of members that have been omitted from the whole groups to form the subgroup. The subgroup formed by omitting various members from the whole group in the list above may, moreover, be an individual member of a whole group such that a carrier, adjuvant and/or additive is provided in the absence of all other members of the whole groups except the selected individual member.

Other uses for or formulations of a composition as provided by this invention are as disclosed in US 2003/062,357; US 2003/079,786; and US 2003/191,047, each of which is incorporated in its entirety as a part hereof.

The present invention is further described in, but not limited by, the following specific embodiments, which illustrate the manufacture of various formulations that incorporate a repellent active ingredient, as described above, as well as certain of the adjuvants, modifiers and/or additives described above.

General Procedures

All reactions and manipulations related to the preparation of active ingredient and formulations were carried out in a standard laboratory fume hood in standard laboratory glassware. Formulation concentrations are reported as weight/weight percentages. Analysis of the repellent active ingredient was performed by GC/MS analysis, and concentration is reported vs. 1,2-dibromobenzene as an internal standard.

EXAMPLE 1

15% w/w Active Lotion

The repellent active ingredient was incorporated into an oil-water emulsion formulation as shown in Table 1. Ingredients in Phase A and B were combined separately at 75° C., then the two phases combined by mixing to uniformity. The resulting mixture of Phases A and B was allowed to cool to 40° C. Phase C (active) was then added slowly over 30 min with rapid mixing agitation. Finally, preservative (Phase D) was added, and the final emulsions then allowed to cool to room temperature, at which they were stored.

TABLE 1

Ingredients for Example 1 lotion formulation

| Phase | Ingredient | Function | INCI Designation | Supplier | % By Weight |
|---|---|---|---|---|---|
| A | Water | Diluent | Water (Aqua) | | 58.35 |
| A | Na2EDTA | Chelating Agent | Disodium EDTA | Akzo | 0.05 |
| A | Jeechem Bugl | Humectant | Butylene Glycol | Jeen Int'l | 2.5 |
| A | MP Diol | Humectant | Methyl-propanediol | Lyondell | 1.5 |
| A | Glycerin 96% | Humectant | Glycerin | Cognis | |
| B | Crodacol C S50 | Emulsion Stabilizer | Cetearyl Alcohol | Croda | |

TABLE 1-continued

Ingredients for Example 1 lotion formulation

| Phase | Ingredient | Function | INCI Designation | Supplier | % By Weight |
|---|---|---|---|---|---|
| B | Brij 721 | Emulsifier | Steareth-21 | Uniqema | 0.5 |
| B | Jeechem Op | Emollient | Ethylhexyl Palmitate | Jeen Int'l | 5 |
| B | Ceraphyl 41 | Emollient | C12-15 Alkyl Lactate | ISP Sutton | 3 |
| B | Polyolpre-polymer 14 | Film Former | PEG-51/Smdi Copolymer | Barnet | 5 |
| B | Finsolv TN | Emollient | C12-15 Alkyl Benzoate | Finetex | 3 |
| B | Cerasynt Q | Emulsifier | Glyceryl Stearate SE | Isp | 2.5 |
| B | Emulsiphos S | Emulsifier | Potassium Cetyl Phosphate Hydrogenated Palm Glycerides | Symrise | 1 |
| B | Rapithix A 60 | Thickener | Sodium Polyacrylate Hydrogenated Polydecene Trideceth-6 | ISP | 1.6 |
| C | Repellent active | Repellent | | DuPont | 15 |
| D | Germazide PMP | Preservative | Phenoxyethanol Chlorphenesin Methylparaben Propylparaben | | 1 |

EXAMPLE 2

15% w/w Active Ingredient Lotion

The repellent active ingredient was incorporated into an oil-water emulsion formulation as shown in Table 2. Ingredients in Phase A and B were combined separately at 75° C., then the two phases combined by mixing to uniformity. The resulting mixture of Phases A and B was allowed to cool to 40° C. Phase C (active) was then added slowly over 30 min with rapid mixing agitation. Finally, preservative (Phase D) was added, and the final emulsions then allowed to cool to room temperature, at which they were stored.

TABLE 2

Ingredients for lotion Example 2 formulation

| Phase | Ingredient (Trade Name) | Function | INCI Designation | Supplier | % By Weight |
|---|---|---|---|---|---|
| A | Water | Diluent | Water (Aqua) | | 49.65 |
| A | Na2EDTA | Chelating Agent | Disodium EDTA | Akzo | 0.05 |
| A | Jeechem Bugl | Humectant | Butylene Glycol | Jeen Int'l | 5 |
| A | MP Diol | Humectant | Methyl-propanediol | Lyondell | 1.5 |
| A | Glycerin 96% | Humectant | Glycerin | Cognis | |
| B | Crodacol C S50 | Emulsion Stabilizer | Cetearyl Alcohol | Croda | |
| B | Brij 721 | Emulsifier | Steareth-21 | Uniqema | 0.7 |
| B | Jeechem Op | Emollient | Ethylhexyl Palmitate | Jeen Int'l | 5 |
| B | Ceraphyl 41 | Emollient | C12-15 Alkyl Lactate | ISP Sutton | 3 |
| B | Polyolpre-polymer 14 | Film Former | PEG-51/Smdi Copolymer | Barnet | 5 |
| B | Finsolv TN | Emollient | C12-15 Alkyl Benzoate | Finetex | 5 |
| B | Cerasynt Q | Emulsifier | Glyceryl Stearate SE | Isp | 2.5 |
| B | Emulsiphos S | Emulsifier | Potassium Cetyl Phosphate Hydrogenated Palm Glycerides | Symrise | 4 |

TABLE 2-continued

Ingredients for lotion Example 2 formulation

| Phase | Ingredient (Trade Name) | Function | INCI Designation | Supplier | % By Weight |
|---|---|---|---|---|---|
| B | Rapithix A 60 | Thickener | Sodium Polyacrylate Hydrogenated Polydecene Trideceth-6 | ISP | 1.6 |
| C | Repellent active | Repellent | | DuPont | 15 |
| D | Germazide PMP | Preservative | Phenoxyethanol Chlorphenesin Methylparaben Propylparaben | | 1 |

EXAMPLE 3

15% w/w Active Lotion

The repellent active ingredient was incorporated into an oil-water emulsion formulation as shown in Table 3. Ingredients in Phase A and B were combined separately at 75° C., then the two phases combined by mixing to uniformity. The resulting mixture of Phases A and B was allowed to cool to 40° C. Phase C (active) was then added slowly over 30 min with rapid mixing agitation. Finally, preservative (Phase D) was added, and the final emulsions then allowed to cool to room temperature, at which they were stored.

TABLE 3

Ingredients for lotion Example 3 formulation

| Phase | Ingredient (Trade Name) | Function | INCI Designation | Supplier | % By Weight |
|---|---|---|---|---|---|
| A | Water | Diluent | Water (Aqua) | | 43.15 |
| A | Na2EDTA | Chelating Agent | Disodium EDTA | Akzo | 0.05 |
| A | Jeechem Bugl | Humectant | Butylene Glycol | Jeen Int'l | 3 |
| A | MP Diol | Humectant | Methylpropanediol | Lyondell | |
| A | Glycerin 96% | Humectant | Glycerin | Cognis | 10 |
| B | Crodacol C S50 | Emulsion Stabilizer | Cetearyl Alcohol | Croda | 1 |
| B | Brij 721 | Emulsifier | Steareth-21 | Uniqema | 0.7 |
| B | Jeechem Op | Emollient | Ethylhexyl Palmitate | Jeen Int'l | 5 |
| B | Ceraphyl 41 | Emollient | C12-15 Alkyl Lactate | ISP Sutton | 3 |
| B | Polyolprepolymer 14 | Film Former | PEG-51/Smdi Copolymer | Barnet | 5 |
| B | Finsolv TN | Emollient | C12-15 Alkyl Benzoate | Finetex | 5 |
| B | Cerasynt Q | Emulsifier | Glyceryl Stearate SE | Isp | 2.5 |
| B | Emulsiphos S | Emulsifier | Potassium Cetyl Phosphate Hydrogenated Palm Glycerides | Symrise | 4 |
| B | Rapithix A 60 | Thickener | Sodium Polyacrylate Hydrogenated Polydecene Trideceth-6 | ISP | 1.6 |
| C | Repellent active | Repellent | | DuPont | 15 |
| D | Germazide PMP | Preservative | Phenoxyethanol Chlorphenesin Methylparaben Propylparaben | | 1 |

EXAMPLE 4

15% w/w Active Alcohol-Based Solution

The repellent active ingredient was incorporated into a liquid alcohol solution, followed by the other ingredients as listed in the Table 4 at a time. After each addition, the solution was allowed to reach uniformity before adding the next ingredient.

TABLE 4

Ingredients for liquid Example 4 formulation

| Ingredient (Trade Name) | Function | INCI Designation | Supplier | % By Weight |
|---|---|---|---|---|
| SD Alcohol 40 2 200 Proof | Diluent | SD Alcohol 40 | Equastar | 57.00 |
| Repellent active | Repellent | PEG-8 Dimethicone | DuPont | 15.00 |
| Zenicone XX | Emollient | PEG-8 Ricinoleate | Zenitech | 5.00 |
| Jeesilc CPS 312 | Emollient | Cyclopentasiloxane | Jeen Int'l | 15.00 |
| Polyolprepolymer 15 | Film Former | PEG-8/SMDI Copolymer | Barnet | 3.00 |
| Eutanol G | Emollient | Octyldodecanol | Cognis | 5.00 |

EXAMPLE 5

15% w/w Active Alcohol-Based Solution

The repellent active ingredient was incorporated into a liquid alcohol solution followed by the other ingredients as listed in the Table 5 one at a time. After each addition, the solution was allowed to reach uniformity before adding the next ingredient.

TABLE 5

Ingredients for liquid Example 5 formulation

| Ingredient (Trade Name) | Function | INCI Designation | Supplier | % By Weight |
|---|---|---|---|---|
| SD Alcohol 40 2 200 Proof | Diluent | SD Alcohol 40 | Equastar | 42.00 |
| Repellent active | Repellent | Butylene glycol | DuPont | 15.00 |
| Jeechem Bugl | Humectant | Methylpropanediol | Jeen Int'l | 5.00 |
| MP Diol | Humectant | Propylene Glycol | Lyondell | 5.00 |

TABLE 5-continued

Ingredients for liquid Example 5 formulation

| Ingredient (Trade Name) | Function | INCI Designation | Supplier | % By Weight |
|---|---|---|---|---|
| Propylene Glycol | Humectant | PEG-8 Dimethicone | Arco | 5.00 |
| Zenicone XX | Emollient | PEG-8 Ricinoleate | Zenitech | 5.00 |
| Jeesilc CPS 312 | Emollient | Cyclopentasiloxane | Jeen Int'l | 15.00 |
| Polyolprepolymer 15 | Film Former | Peg-8/Smdi Copolymer | Barnet | 3.00 |
| Eutanol G | Emollient | Octyldodecanol | Cognis | 5.00 |

EXAMPLE 6

15% w/w Active Alcohol-Based Solution

The repellent active ingredient was incorporated into a liquid alcohol solution followed by the other ingredients as listed in the Table 6 one at a time. After each addition, the solution was allowed to reach uniformity before adding the next ingredient.

TABLE 6

Ingredients for liquid Example 6 formulation

| Ingredient (Trade Name) | Function | INCI Designation | Supplier | % By Weight |
|---|---|---|---|---|
| SD Alcohol 40 2 200 Proof | Diluent | SD Alcohol 40 | Equastar | 37.00 |
| Repellent active | Repellent | Isostearyl Neopentanoate | DuPont | 15.00 |
| Jeechem Bugl | Humectant | Methylpropanediol | Jeen Int'l | 15.00 |
| MP Diol | Humectant | Methylpropanediol | Lyondell | 5.00 |
| Glycerin 96% | Humectant | Glycerin | Cognis | 10.00 |
| Zenicone XX | Emollient | PEG-8 Dimethicone PEG-8 Ricinoleate | Zenitech | 5.00 |
| Jeesilc CPS 312 | Emollient | Cyclopentasiloxane | Jeen Int'l | 5.00 |
| Polyolprepolymer 15 | Film Former | PEG-8/SMDI Copolymer | Barnet | 3.00 |
| Eutanol G | Emollient | Octyldodecanol | Cognis | 5.00 |

Formulations similar to those described above were tested on human subjects for repellent efficacy against mosquitoes in the field, and in arm-in-cage tests in a laboratory; and were tested for repellent efficacy against blackflies in field tests. All test results indicated that the formulations provided desirably high levels of repellent protection.

A formulated composition herein may include any one or more or all of the different kinds of cosmetic adjuvants, modifiers and additives in the total group thereof disclosed above. The adjuvants, modifiers and additives may also, however, be any one or more of those members of a subgroup of the total group of adjuvants, modifiers and additives disclosed herein, where the subgroup is formed by excluding any one or more other members from the total group. As a result, the adjuvants, modifiers and additives in such instance may not only be any one or more of the adjuvants, modifiers and additives in any subgroup of any size that may be selected from the total group thereof in all the various different combinations of individual members of the total group, but the members in any subgroup may thus be used in the absence of the one or more of the members of the total group that have been excluded to form the subgroup. The subgroup formed by excluding various members from the total group of adjuvants, modifiers and additives may, moreover, be an individual member of the total group such that the adjuvant, modifier or additive is used in the absence of all other members of the total group except the selected individual member.

With respect to a particular cosmetic adjuvant, modifier or additive, a formulated composition herein may include any one or more or all of the different kinds of materials in the total group thereof described above as providing the desired properties or function of that adjuvant, modifier or additive. The materials may also, however, be any one or more of those members of a subgroup of the total group of materials disclosed herein for the particular adjuvant, modifier or additive, where the subgroup is formed by excluding any one or more other members from the total group. As a result, the materials in such instance may not only be any one or more of the adjuvant/modifier/additive materials in any subgroup of any size that may be selected from the total group thereof in all the various different combinations of individual members of the total group, but the members in any subgroup may thus be used in the absence of the one or more of the members of the total group that have been excluded to form the subgroup. The subgroup formed by excluding various members from the total group of materials may, moreover, be an individual member of the total group such that the adjuvant/modifier/additive material is used in the absence of all other members of the total group except the selected individual member.

Certain features of this invention are described herein in the context of an embodiment that combines various such features together, whether as described in the disclosure or in one of the examples. The scope of the invention is not, however, limited by the description of only certain features within any particular embodiment, and the invention also includes (1) a subcombination of fewer than all of the features of any described embodiment, which subcombination is characterized by the absence of the features omitted to form the subcombination; (2) each of the features, individually, included within the combination of the described embodiment; and (3) other combinations of features formed from one or more or all of the features of the described embodiment together with other features as disclosed elsewhere herein.

In this specification, unless explicitly stated otherwise or indicated to the contrary by the context of usage, where an embodiment of this invention is stated or described as comprising, including, containing, having, being composed of or being constituted by or of certain features or elements, one or more features or elements in addition to those explicitly stated or described may be present in the embodiment. An alternative embodiment of this invention, however, may be stated or described as consisting essentially of certain features or elements, in which embodiment features or elements that would materially alter the principle of operation or the distinguishing characteristics of the embodiment are not present therein. A further alternative embodiment of this invention may be stated or described as consisting of certain features or elements, in which embodiment, or in insubstantial variations thereof, only the features or elements specifically stated or described are present.

What is claimed is:

1. A composition comprising in admixture
   (a) a dihydronepetalactone ;
   (b) water;
   (c) a component (c) comprising polyoxyethylene ether of steary alcohol;
   glyceral stearate; potassium cetyl phosphate; and hydrogenated palm glyceride;
   (d) a component (d) comprising cetearyl alcohol;
   (e) a component (e) comprising butylene glycol, methylpropane diol, and glycerin; and
   (f) a component (f) comprising sodium polyacrylate, hydrogenated polydecene and $C_{16}$~$C_{24}$ polyethylene glycol ethers of decyl alcohol;

wherein the composition comprises the component (a) in an amount in the range of from about 0.01 wt% to about 20 wt% based on the total weight of the total composition.

2. A composition according to claim 1 further comprising one or more of the components selected from the group consisting of (g) a chelating agent, (h) a preservative, (i) a film former, and (j) an emollient.

3. A composition according to claim 1 further comprising one or more of the components selected from the group consisting of (k) a fragrance, (l) a sunscreen agent, (m) an antioxidant, (n) a UV absorber, (o) a biocide, and (p) an essential oil.

4. A composition according to claim 2 wherein the film former is selected from the group consisting of a polymer and a copolymer.

5. A composition according to claim 2 wherein the emollient is selected from the group consisting of $C_4$–$C_{20}$ linear or branched aliphatic esters of $C_{10}$–$C_{30}$ carboxylic acids.

6. A composition according to claim 1 which is formulated as a lotion, cream or gel.

7. A method of repelling one or more ticks or insects comprising exposing the tick(s) and/or insect(s) to a composition according to claim 1.

8. A method according to claim 7 which comprises applying a composition according to claim 1 to a surface of a host for the tick(s) and/or insect(s).

9. A composition comprising in admixture
(a) a dihydronepetalactone;
(b) an alcohol;
(c) a component (c) comprising butylene glycol, methylpropane diol, and propylene glycol;
(d) a component (d) comprising cyclopentasiloxane and octyldodecanol; and
(e) a component (e) comprising a copolymer of diethylene glycol;
wherein the composition comprises the component (a) in an amount in the range of from about 0.01 wt% to about 20 wt% based on the total weight of the total composition.

10. A composition according to claim 9 further comprising one or more of the components selected from the group consisting of (f) a fragrance, (g) a sunscreen agent, (h) an antioxidant, (i) a UV absorber, (j) a biocide, and (k) an essential oil.

11. A composition according to claim 9 which is formulated as a sprayable liquid.

12. A method of repelling one or more ticks or insects comprising exposing the tick(s) and/or insect(s) to a composition according to claim 9.

13. A method according to claim 12 which comprises applying a composition according to claim 9 to a surface of a host for the tick(s) and/or insect(s).

* * * * *